United States Patent
Seehra et al.

(10) Patent No.: US 12,404,313 B2
(45) Date of Patent: Sep. 2, 2025

(54) GDNF FUSION POLYPEPTIDES AND METHODS OF USE THEREOF

(71) Applicant: Keros Therapeutics, Inc., Lexington, MA (US)

(72) Inventors: Jasbir S. Seehra, Lexington, MA (US); Jennifer Lachey, Lincoln, MA (US)

(73) Assignee: Keros Therapeutics, Inc., Lexington, MA (US)

( * ) Notice: Subject to any disclaimer, the term of this patent is extended or adjusted under 35 U.S.C. 154(b) by 0 days.

(21) Appl. No.: 18/443,769

(22) Filed: Feb. 16, 2024

(65) Prior Publication Data
US 2024/0209048 A1 Jun. 27, 2024

Related U.S. Application Data

(62) Division of application No. 16/348,982, filed as application No. PCT/US2017/060953 on Nov. 9, 2017, now Pat. No. 11,912,750.

(60) Provisional application No. 62/420,480, filed on Nov. 10, 2016.

(51) Int. Cl.
| | |
|---|---|
| C07K 14/475 | (2006.01) |
| A61K 38/00 | (2006.01) |
| A61P 3/04 | (2006.01) |
| A61P 3/10 | (2006.01) |
| A61P 25/00 | (2006.01) |
| C07K 14/47 | (2006.01) |
| C07K 14/765 | (2006.01) |
| C07K 14/78 | (2006.01) |
| C07K 19/00 | (2006.01) |

(52) U.S. Cl.
CPC ............ *C07K 14/4756* (2013.01); *A61P 3/04* (2018.01); *A61P 3/10* (2018.01); *A61P 25/00* (2018.01); *C07K 14/4702* (2013.01); *C07K 14/475* (2013.01); *C07K 14/765* (2013.01); *C07K 14/78* (2013.01); *C07K 19/00* (2013.01); *A61K 38/00* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | |
|---|---|---|
| 5,641,749 A | 6/1997 | Yan et al. |
| 5,641,750 A | 6/1997 | Louis |
| 5,731,284 A | 3/1998 | Williams |
| 5,733,875 A | 3/1998 | Martin |
| 5,736,516 A | 4/1998 | Louis |
| 5,741,778 A | 4/1998 | Martin et al. |
| 5,837,681 A | 11/1998 | Magal |
| 5,929,041 A | 7/1999 | Magal |
| 6,015,572 A | 1/2000 | Lin et al. |
| 6,093,802 A | 7/2000 | Lin et al. |
| 6,184,200 B1 | 2/2001 | Hu |
| 6,221,376 B1 | 4/2001 | Lin et al. |
| 6,362,319 B1 | 3/2002 | Lin et al. |
| 6,455,277 B1 | 9/2002 | Fox et al. |
| 7,138,251 B1 | 11/2006 | Fox et al. |
| 7,160,924 B2 | 1/2007 | Kinstler et al. |
| 7,226,758 B1 | 6/2007 | Lin et al. |
| 7,390,781 B2 | 6/2008 | Hu |
| 7,611,865 B2 | 11/2009 | Hu |
| 7,741,446 B2 | 6/2010 | Pardridge et al. |
| 8,946,151 B2 | 2/2015 | Gill et al. |
| 8,946,152 B2 | 2/2015 | Gill et al. |
| 11,912,750 B2 | 2/2024 | Seehra et al. |
| 2002/0197675 A1 | 12/2002 | Lin et al. |
| 2004/0175795 A1 | 9/2004 | Lin et al. |
| 2004/0253247 A1 | 12/2004 | Dennis et al. |
| 2004/0254114 A1 | 12/2004 | Hu |
| 2006/0166325 A1 | 7/2006 | Fox et al. |
| 2011/0045007 A1 | 2/2011 | Schuurman et al. |
| 2011/0251267 A1 | 10/2011 | Hu |
| 2012/0196803 A1 | 8/2012 | Demeule et al. |
| 2012/0276043 A1 | 11/2012 | Yang et al. |
| 2014/0113370 A1 | 4/2014 | Camphausen et al. |
| 2015/0064185 A1 | 3/2015 | Holt et al. |

FOREIGN PATENT DOCUMENTS

| | | |
|---|---|---|
| JP | 2781459 B2 | 7/1998 |
| JP | 2007-289200 A | 11/2007 |
| JP | 2009-504164 A | 2/2009 |
| JP | 2012-529272 A | 11/2012 |
| WO | WO-96/14861 A1 | 5/1996 |

(Continued)

OTHER PUBLICATIONS

Zhang et al., Progress in Neurobiology 204 (2021) 102089 (Year: 2021).*
Boado et al., "GDNF fusion protein for targeted-drug delivery across the human blood-brain barrier," Biotechnol Bioeng. 100(2):387-96 (2008).
International Search Report and Written Opinion for International Application No. PCT/US17/60953, mailed Mar. 29, 2018 (17 pages).
Mwangi et al., "Glial cell line-derived neurotrophic factor protects against high-fat diet-induced obesity," Am J Physiol Gastrointest Liver Physiol, 306(6):G515-25 (2014).
Ohshima-Hosoyama et al., "A Monoclonal Antibody-GDNF Fusion Protein Is Not Neuroprotective and Is Associated with Proliferative Pancreatic Lesions in Parkinsonian Monkeys," PLoS One. 7(6):e39036 (2012).

(Continued)

*Primary Examiner* — Christina M Borgeest
(74) *Attorney, Agent, or Firm* — Clark & Elbing LLP

(57) ABSTRACT

The present invention relates to compositions and methods of GDNF fusion polypeptides, wherein the GDNF fusion polypeptides include an Fc domain, an albumin-binding peptide, a fibronectin domain, or a human serum albumin, joined to a GDNF variant either directly or by the way of a linker. The GDNF fusion polypeptides may used to treat metabolic diseases, such as obesity and Type-1 and Type-2 diabetes, and neurological diseases, such as Amyotrophic lateral sclerosis (ALS) and Parkinson's disease.

15 Claims, 7 Drawing Sheets

Specification includes a Sequence Listing.

(56) References Cited

FOREIGN PATENT DOCUMENTS

| WO | WO-96/33731 A1 | 10/1996 |
|---|---|---|
| WO | WO-97/11964 A1 | 4/1997 |
| WO | WO-97/11965 A1 | 4/1997 |
| WO | WO-97/19693 A1 | 6/1997 |
| WO | WO-97/19694 A1 | 6/1997 |
| WO | WO-97/19695 A1 | 6/1997 |
| WO | WO-97/30722 A1 | 8/1997 |
| WO | WO-97/34567 A2 | 9/1997 |
| WO | WO-97/40152 A1 | 10/1997 |
| WO | WO-98/54213 A2 | 12/1998 |
| WO | WO-00/034475 A3 | 11/2000 |
| WO | WO-2005/003296 A2 | 1/2005 |
| WO | WO-2006/044115 A2 | 4/2006 |
| WO | WO-2009/070597 A2 | 6/2009 |
| WO | WO-2010/142035 A1 | 12/2010 |
| WO | WO-2015/073727 A1 | 5/2015 |
| WO | WO-2015/143199 A1 | 9/2015 |

OTHER PUBLICATIONS

Tümer et al., "Hypothalamic rAAV-mediated GDNF gene delivery ameliorates age-related obesity," Neurobiol Aging 27(3):459-70 (2006).

Zhou et al., "Monoclonal antibody-glial-derived neurotrophic factor fusion protein penetrates the blood-brain barrier in the mouse," Drug Metab Dispos. 38(4):566-72 (2010).

Jafarlou et al., "An overview of the history, applications, advantages, disadvantages and prospects of gene therapy," J Biol Regul Homeost Agents. 30(2):315-21 (2016).

Wang et al., "New insights into the altered fibronectin matrix and extrasynaptic transmission in the aging brain," J Clin Gerontology and Geriatrics 2:35-41 (2011).

Winkler et al., "Oligonucleotide conjugates for therapeutic applications," Ther Deliv 4(7):791-809 (2013).

Kang et al., "Protein engineering, expression, and activity of a novel fusion protein possessing keratinocyte growth factor 2 and fibronectin," Acta Biochim Biophys Sin (Shanghai).41(1):16-20 (2009).

Phillips, "The challenge of gene therapy and DNA delivery," J Pharm Pharmacol. 53(9):1169-74 (2001).

Jacobs et al., "Fusion to a highly stable consensus albumin binding domain allows for tunable pharmacokinetics," Protein Eng Des Sel. 28(10):385-93 (2015).

Bhattacharya et al., "Impact of genetic variation on three dimensional structure and function of proteins," PLoS One 12(3):e0171355 (Mar. 2017) (22 pages).

Yaden et al., "Follistatin: A Novel Therapeutic for the Improvement of Muscle Regeneration," J Pharmacol Exp Ther. 349(2):355-71(2014).

Zhang et al., "Combined Administration of a Novel Mutant TGF-beta1/Fc and Rapamycin Promotes Induction of Regulatory T Cells and Islet Allograft Tolerance," J Immunol. 185(8):4750-9 (2010).

Cik et al., "Binding of GDNF and Neurturin to Human GDNF Family Receptor alpha 1 and 2," J Biol Chem. 275(36):27505-12 (2000).

Wolfman et al., "Activation of latent myostatin by the BMP-1/tolloid family of metalloproteinases," Proc Natl Acad Sci U S A. 100(26):15842-6 (2003).

Sengle et al., "Prodomains of transforming growth factor beta(TGFbeta) superfamily members specify different functions: extracellular matrix interactions and growth factor bioavailability," J Biol Chem. 286(7):5087-99 (2011).

Ultee, "Therapeutic Fc-Fusion Proteins," mAbs. 6(4):810-811 (2014).

Rath et al., "Fc-fusion proteins and FcRn: structural insights for longer-lasting and more effective therapeutics," Crit Rev Biotechnol. 35(2):235-254 (2015).

Xiao et al., "Receptor-mediated endocytosis and brain delivery of therapeutic biologics," Int J Cell Biol. 2013:703545 (2013) (15 pages).

Saarma, Mart., "GDNF—a stranger in the TGF-beta superfamily?" Eur J Biochem. 267(24):6968-71 (2000).

Strohl, "Fusion Proteins for Half-Life Extension of Biologics as a Strategy to Make Biobetters," BioDrugs. 29(4):215-239 (2015).

Ying et al., "Soluble monomeric IgG1 Fc," J Biol Chem. 287(23):19399-408 (Jun. 1, 2012).

To et al., "Plasma and cellular fibronectin: distinct and independent functions during tissue repair," Fibrogenesis Tissue Repair. 4:21. doi: 10.1186/1755-1536-4-21 (Sep. 16, 2011) (17 pages).

Chichili et al., "Linkers in the structural biology of protein-protein interactions," Protein Sci. 22:153-167 (2013).

Tokmakov et al., "Multiple Post-translational Modifications Affect Heterologous Protein Synthesis," J of Bio Chem. 287(32): 27106-27116 (Aug. 2012) (11 pages).

Sariola and Saarma, "Novel Functions and Signalling Pathways for Gdnf," J of Cell Sci. 116(Pt 19):3855-3862 (2003) (8 pages).

Adams et al., "A two-site flexible clamp mechanism for RET-GDNF-GFRalpha1 assembly reveals both conformational adaptation and strict geometric spacing," Structure. 29(7):694-708.e7 (Jul. 2021) (23 pages).

Anitha et al. "GDNF rescues hyperglycemia-induced diabetic enteric neuropathy through activation of the PI3K/Akt pathway," Journal of Clinical Investigation. 116(2): 344-356 (14 pages) (Feb. 2006).

Hong et al. "GDNF therapy for Parkinson's disease," Expert Rev. Neurother. 8(7): 1125-1139 (2008).

Klein et al. "GDNF Delivery Using Human Neural Progenitor Cells in a Rat Model of ALS," Human Gene Therapy. 16: 509-521 (22 pages) (Apr. 2005).

Revilla et al. "Lenti-GDNF Gene Therapy Protects Against Alzheimer's Disease-Like Neuropathology in 3xTg-AD Mice and MC65 Cells," CNS Neuroscience and Therapeutics. 20: 961-972 (2014).

\* cited by examiner

SEQUENCE LISTING

```
Sequence total quantity: 37
SEQ ID NO: 1            moltype = AA  length = 211
FEATURE                 Location/Qualifiers
source                  1..211
                        mol_type = protein
                        organism = Homo sapiens
SEQUENCE: 1
MKLWDVVAVC LVLLHTASAF PLPAGKRPPE APAEDRSLGR RRAPFALSSD SNMPEDYPDQ   60
FDDVMDFIQA TIKRLKRSPD KQMAVLPRRE RNRQAAAANP ENSRGKGRRG QRGKNRGCVL  120
TAIHLNVTDL GLGYETKEEL IFRYCSGSCD AAETTYDKIL KNLSRNRRLV SDKVGQACCR  180
PIAFDDDLSF LDDNLVYHIL RKHSAKRCGC I                                 211

SEQ ID NO: 2            moltype = AA  length = 11
FEATURE                 Location/Qualifiers
source                  1..11
                        mol_type = protein
                        organism = synthetic construct
SEQUENCE: 2
DICLPRWGCL W                                                        11

SEQ ID NO: 3            moltype = AA  length = 246
FEATURE                 Location/Qualifiers
source                  1..246
                        mol_type = protein
                        organism = Homo sapiens
SEQUENCE: 3
MEWSWVFLFF LSVTTGVHSD KTHTCPPCPA PELLGGPSVF LFPPKPKDTL MISRTPEVTC   60
VVVDVSHEDP EVKFNWYVDG VEVHNAKTKP REEQYNSTYR VVSVLTVLHQ DWLNGKEYKC  120
KVSNKALPAP IEKTISKAKG QPREPQVYTL PPSRDELTKN QVSLTCLVKG FYPSDIAVEW  180
ESNGQPENNY KTTPPVLDSD GSFFLYSKLT VDKSRWQQGN VFSCSVMHEA LHNHYTQKSL  240
```

```
SLSPGK                                                                            246

SEQ ID NO: 4           moltype =    length =
SEQUENCE: 4
000

SEQ ID NO: 5           moltype = AA   length = 5
FEATURE                Location/Qualifiers
source                 1..5
                       mol_type = protein
                       organism = synthetic construct
SEQUENCE: 5
GGGGS                                                                             5

SEQ ID NO: 6           moltype = AA   length = 4
FEATURE                Location/Qualifiers
source                 1..4
                       mol_type = protein
                       organism = synthetic construct
SEQUENCE: 6
GGSG                                                                              4

SEQ ID NO: 7           moltype = AA   length = 4
FEATURE                Location/Qualifiers
source                 1..4
                       mol_type = protein
                       organism = synthetic construct
SEQUENCE: 7
SGGG                                                                              4

SEQ ID NO: 8           moltype = AA   length = 4
FEATURE                Location/Qualifiers
source                 1..4
                       mol_type = protein
                       organism = synthetic construct
SEQUENCE: 8
GSGS                                                                              4

SEQ ID NO: 9           moltype = AA   length = 6
FEATURE                Location/Qualifiers
source                 1..6
                       mol_type = protein
                       organism = synthetic construct
SEQUENCE: 9
GSGSGS                                                                            6

SEQ ID NO: 10          moltype = AA   length = 8
FEATURE                Location/Qualifiers
source                 1..8
                       mol_type = protein
                       organism = synthetic construct
SEQUENCE: 10
GSGSGSGS                                                                          8

SEQ ID NO: 11          moltype = AA   length = 10
FEATURE                Location/Qualifiers
source                 1..10
                       mol_type = protein
                       organism = synthetic construct
SEQUENCE: 11
GSGSGSGSGS                                                                        10

SEQ ID NO: 12          moltype = AA   length = 12
FEATURE                Location/Qualifiers
source                 1..12
                       mol_type = protein
                       organism = synthetic construct
SEQUENCE: 12
GSGSGSGSGS GS                                                                     12

SEQ ID NO: 13          moltype = AA   length = 6
FEATURE                Location/Qualifiers
source                 1..6
                       mol_type = protein
                       organism = synthetic construct
SEQUENCE: 13
GGSGGS                                                                            6

SEQ ID NO: 14          moltype = AA   length = 9
```

```
FEATURE              Location/Qualifiers
source               1..9
                     mol_type = protein
                     organism = synthetic construct
SEQUENCE: 14
GGSGGSGGS                                                                   9

SEQ ID NO: 15        moltype = AA  length = 12
FEATURE              Location/Qualifiers
source               1..12
                     mol_type = protein
                     organism = synthetic construct
SEQUENCE: 15
GGSGGSGGSG GS                                                              12

SEQ ID NO: 16        moltype = AA  length = 4
FEATURE              Location/Qualifiers
source               1..4
                     mol_type = protein
                     organism = synthetic construct
SEQUENCE: 16
GGSG                                                                        4

SEQ ID NO: 17        moltype = AA  length = 4
FEATURE              Location/Qualifiers
source               1..4
                     mol_type = protein
                     organism = synthetic construct
SEQUENCE: 17
GGSG                                                                        4

SEQ ID NO: 18        moltype = AA  length = 8
FEATURE              Location/Qualifiers
source               1..8
                     mol_type = protein
                     organism = synthetic construct
SEQUENCE: 18
GGSGGGSG                                                                    8

SEQ ID NO: 19        moltype = AA  length = 12
FEATURE              Location/Qualifiers
source               1..12
                     mol_type = protein
                     organism = synthetic construct
SEQUENCE: 19
GGSGGGSGGG SG                                                              12

SEQ ID NO: 20        moltype = AA  length = 5
FEATURE              Location/Qualifiers
source               1..5
                     mol_type = protein
                     organism = synthetic construct
SEQUENCE: 20
GGGGS                                                                       5

SEQ ID NO: 21        moltype = AA  length = 15
FEATURE              Location/Qualifiers
source               1..15
                     mol_type = protein
                     organism = synthetic construct
SEQUENCE: 21
GGGGSGGGGS GGGGS                                                           15

SEQ ID NO: 22        moltype = AA  length = 9
FEATURE              Location/Qualifiers
source               1..9
                     mol_type = protein
                     organism = synthetic construct
SEQUENCE: 22
GGGGAGGGG                                                                   9

SEQ ID NO: 23        moltype = AA  length = 10
FEATURE              Location/Qualifiers
source               1..10
                     mol_type = protein
                     organism = synthetic construct
SEQUENCE: 23
GENLYFQSGG                                                                 10
```

-continued

```
SEQ ID NO: 24            moltype = AA   length = 8
FEATURE                  Location/Qualifiers
source                   1..8
                         mol_type = protein
                         organism = synthetic construct
SEQUENCE: 24
SACYCELS                                                                          8

SEQ ID NO: 25            moltype = AA   length = 5
FEATURE                  Location/Qualifiers
source                   1..5
                         mol_type = protein
                         organism = synthetic construct
SEQUENCE: 25
RSIAT                                                                             5

SEQ ID NO: 26            moltype = AA   length = 17
FEATURE                  Location/Qualifiers
source                   1..17
                         mol_type = protein
                         organism = synthetic construct
SEQUENCE: 26
RPACKIPNDL KQKVMNH                                                               17

SEQ ID NO: 27            moltype = AA   length = 36
FEATURE                  Location/Qualifiers
source                   1..36
                         mol_type = protein
                         organism = synthetic construct
SEQUENCE: 27
GGSAGGSGSG SSGGSSGASG TGTAGGTGSG SGTGSG                                           36

SEQ ID NO: 28            moltype = AA   length = 17
FEATURE                  Location/Qualifiers
source                   1..17
                         mol_type = protein
                         organism = synthetic construct
SEQUENCE: 28
AAANSSIDLI SVPVDSR                                                               17

SEQ ID NO: 29            moltype = AA   length = 36
FEATURE                  Location/Qualifiers
source                   1..36
                         mol_type = protein
                         organism = synthetic construct
SEQUENCE: 29
GGSGGGSEGG GSEGGGSEGG GSEGGGSEGG GSGGGS                                           36

SEQ ID NO: 30            moltype = AA   length = 93
FEATURE                  Location/Qualifiers
source                   1..93
                         mol_type = protein
                         organism = Homo sapiens
SEQUENCE: 30
GPVEVFITET PSQPNSHPIQ WNAPQPSHIS KYILRWRPKN SVGRWKEATI PGHLNSYTIK                  60
GLKPGVVYEG QLISIQQYGH QEVTRFDFTT TST                                              93

SEQ ID NO: 31            moltype = AA   length = 609
FEATURE                  Location/Qualifiers
source                   1..609
                         mol_type = protein
                         organism = Homo sapiens
SEQUENCE: 31
MKWVTFISLL FLFSSAYSRG VFRRDAHKSE VAHRFKDLGE ENFKALVLIA FAQYLQQCPF                  60
EDHVKLVNEV TEFAKTCVAD ESAENCDKSL HTLFGDKLCT VATLRETYGE MADCCAKQEP                 120
ERNECFLQHK DDNPNLPRLV RPEVDVMCTA FHDNEETFLK KYLYEIARRH PYFYAPELLF                 180
FAKRYKAAFT ECCQAADKAA CLLPKLDELR DEGKASSAKQ RLKCASLQKF GERAFKAWAV                 240
ARLSQRFPKA EFAEVSKLVT DLTKVHTECC HGDLLECADD RADLAKYICE NQDSISSKLK                 300
ECCEKPLLEK SHCIAEVEND EMPADLPSLA ADFVESKDVC KNYAEAKDVF LGMFLYEYAR                 360
RHPDYSVVLL LRLAKTYETT LEKCCAAADP HECYAKVFDE FKPLVEEPQN LIKQNCELFE                 420
QLGEYKFQNA LLVRYTKKVP QVSTPTLVEV SRNLGKVGSK CCKHPEAKRM PCAEDYLSVV                 480
LNQLCVLHEK TPVSDRVTKC CTESLVNRRP CFSALEVDET YVPKEFNAET FTFHADICTL                 540
SEKERQIKKQ TALVELVKHK PKATKEQLKA VMDDFAAFVE KCCKADDKET CFAEEGKKLV                 600
AASQAALGL                                                                       609

SEQ ID NO: 32            moltype = AA   length = 380
FEATURE                  Location/Qualifiers
source                   1..380
                         mol_type = protein
```

```
                         organism = synthetic construct
SEQUENCE: 32
MEWSWVFLFF LSVTTGVHSD KTHTCPPCPA PELLGGPSVF LFPPKPKDTL MISRTPEVTC    60
VVVDVSHEDP EVKFNWYVDG VEVHNAKTKP REEQYNSTYR VVSVLTVLHQ DWLNGKEYKC   120
KVSNKALPAP IEKTISKAKG QPREPQVYTL PPSRDELTKN QVSLTCLVKG FYPSDIAVEW   180
ESNGQPENNY KTTPPVLDSD GSFFLYSKLT VDKSRWQQGN VFSCSVMHEA LHNHYTQKSL   240
SLSPGKSPDK QMAVLPRRER NRQAAAANPE NSRGKGRRGQ RGKNRGCVLT AIHLNVTDLG   300
LGYETKEELI FRYCSGSCDA AETTYDKILK NLSRNRRLVS DKVGQACCRP IAFDDDLSFL   360
DDNLVYHILR KHSAKRCGCI                                               380

SEQ ID NO: 33            moltype = AA  length = 369
FEATURE                  Location/Qualifiers
source                   1..369
                         mol_type = protein
                         organism = synthetic construct
SEQUENCE: 33
MEWSWVFLFF LSVTTGVHSD KTHTCPPCPA PELLGGPSVF LFPPKPKDTL MISRTPEVTC    60
VVVDVSHEDP EVKFNWYVDG VEVHNAKTKP REEQYNSTYR VVSVLTVLHQ DWLNGKEYKC   120
KVSNKALPAP IEKTISKAKG QPREPQVYTL PPSRDELTKN QVSLTCLVKG FYPSDIAVEW   180
ESNGQPENNY KTTPPVLDSD GSFFLYSKLT VDKSRWQQGN VFSCSVMHEA LHNHYTQKSL   240
SLSPGKGGGN RQAAAANPEN SRGKGRRGQR GKNRGCVLTA IHLNVTDLGL GYETKEELIF   300
RYCSGSCDAA ETTYDKILKN LSRNRRLVSD KVGQACCRPI AFDDDLSFLD DNLVYHILRK   360
HSAKRCGCI                                                           369

SEQ ID NO: 34            moltype = AA  length = 351
FEATURE                  Location/Qualifiers
source                   1..351
                         mol_type = protein
                         organism = synthetic construct
SEQUENCE: 34
MEWSWVFLFF LSVTTGVHSD KTHTCPPCPA PELLGGPSVF LFPPKPKDTL MISRTPEVTC    60
VVVDVSHEDP EVKFNWYVDG VEVHNAKTKP REEQYNSTYR VVSVLTVLHQ DWLNGKEYKC   120
KVSNKALPAP IEKTISKAKG QPREPQVYTL PPSRDELTKN QVSLTCLVKG FYPSDIAVEW   180
ESNGQPENNY KTTPPVLDSD GSFFLYSKLT VDKSRWQQGN VFSCSVMHEA LHNHYTQKSL   240
SLSPGKGGGG QRGKNRGCVL TAIHLNVTDL GLGYETKEEL IFRYCSGSCD AAETTYDKIL   300
KNLSRNRRLV SDKVGQACCR PIAFDDDLSF LDDNLVYHIL RKHSAKRCGC I            351

SEQ ID NO: 35            moltype = AA  length = 344
FEATURE                  Location/Qualifiers
source                   1..344
                         mol_type = protein
                         organism = synthetic construct
SEQUENCE: 35
MEWSWVFLFF LSVTTGVHSD KTHTCPPCPA PELLGGPSVF LFPPKPKDTL MISRTPEVTC    60
VVVDVSHEDP EVKFNWYVDG VEVHNAKTKP REEQYNSTYR VVSVLTVLHQ DWLNGKEYKC   120
KVSNKALPAP IEKTISKAKG QPREPQVYTL PPSRDELTKN QVSLTCLVKG FYPSDIAVEW   180
ESNGQPENNY KTTPPVLDSD GSFFLYSKLT VDKSRWQQGN VFSCSVMHEA LHNHYTQKSL   240
SLSPGKGGGG CVLTAIHLNV TDLGLGYETK EELIFRYCSG SCDAAETTYD KILKNLSRNR   300
RLVSDKVGQA CCRPIAFDDD LSFLDDNLVY HILRKHSAKR CGCI                    344

SEQ ID NO: 36            moltype = AA  length = 350
FEATURE                  Location/Qualifiers
source                   1..350
                         mol_type = protein
                         organism = synthetic construct
SEQUENCE: 36
MEWSWVFLFF LSVTTGVHSD KTHTCPPCPA PELLGGPSVF LFPPKPKDTL MISRTPEVTC    60
VVVDVSHEDP EVKFNWYVDG VEVHNAKTKP REEQYNSTYR VVSVLTVLHQ DWLNGKEYKC   120
KVSNKALPAP IEKTISKAKG QPREPQVYTL PPSRDELTKN QVSLTCLVKG FYPSDIAVEW   180
ESNGQPENNY KTTPPVLDSD GSFFLYSKLT VDKSRWQQGN VFSCSVMHEA LHNHYTQKSL   240
SLSPGKGGGG AGGGGGCVLT AIHLNVTDLG LGYETKEELI FRYCSGSCDA AETTYDKILK   300
NLSRNRRLVS DKVGQACCRP IAFDDDLSFL DDNLVYHILR KHSAKRCGCI              350

SEQ ID NO: 37            moltype = AA  length = 334
FEATURE                  Location/Qualifiers
source                   1..334
                         mol_type = protein
                         organism = synthetic construct
SEQUENCE: 37
MEWSWVFLFF LSVTTGVHSA PELLGGPSVF LFPPKPKDTL MISRTPEVTC VVVDVSHEDP    60
EVKFNWYVDG VEVHNAKTKP REEQYNSTYR VVSVLTVLHQ DWLNGKEYKC KVSNKALPAP   120
IEKTISKAKG QPREPQVYTL PPSRDELTKN QVSLWCLVKG FYPSDIAVEW ESNGQPENNY   180
KTTPPVLDSD GSFFLYSKLT VDKSRWQQGN VFSCSVMHEA LHNHYTQKSL SLSPGKGGGG   240
CVLTAIHLNV TDLGLGYETK EELIFRYCSG SCDAAETTYD KILKNLSRNR RLVSDKVGQA   300
CCRPIAFDDD LSFLDDNLVY HILRKHSAKR CGCI                               334
```

GDNF FUSION POLYPEPTIDES AND METHODS OF USE THEREOF

SEQUENCE LISTING

The instant application contains a Sequence Listing which has been submitted electronically in XML file format and is hereby incorporated by reference in its entirety. Said XML copy, created on Feb. 9, 2024, is named 51184-003003_Sequence_Listing_2_9_24.xml and is 35,429 bytes in size.

BACKGROUND OF THE INVENTION

Obesity is an increasing problem in the United States, with a prevalence of approximately 25% of the population. Increased visceral and subcutaneous fat causes dysfunction of various organs. Excessive body weight is a risk factor for any array of complications, including obesity, diabetes (e.g., Type-1 and Type-2 diabetes), cardiovascular disease, and several forms of cancer.

Insulin resistance occurs when peripheral tissues require an elevated amount of insulin and is associated with obesity. Once pancreatic β cells can no longer produce sufficient insulin to meet the demand, hyperglycemia occurs and Type-2 diabetes develops. Adipocytes, which are increased in obesity, are believed to play a role in this process. Efforts to treat obesity and its related diseases and conditions, including metabolic diseases (especially Type-1 and Type-2 diabetes) and insulin resistance, have taken varying approaches ranging from surgery to pharmaceuticals.

Despite the prevalence of obesity and metabolic diseases such as diabetes (e.g., Type-1 and Type-2 diabetes), few therapeutic options are available. There exists a need for novel treatments for these metabolic diseases.

SUMMARY OF THE INVENTION

The present invention features glial-derived neurotrophic factor (GDNF) fusion polypeptides that include an Fc domain, an albumin-binding peptide, a fibronectin domain, or a human serum albumin joined to the N-terminus of a GDNF variant directly or by way of a linker. The GDNF fusion polypeptides of the invention bind to human GDNF family receptor alpha-1 (GFRα1) and desirably have long serum half-life. The invention also features pharmaceutical compositions and methods of using these GDNF fusion polypeptides to treat and/or prevent metabolic diseases such as obesity and Type-1 and Type-2 diabetes, and neurological diseases such as schizophrenia, epilepsy, Amyotrophic lateral sclerosis (ALS), Parkinson's disease, Alzheimer's disease, Huntington's disease, anxiety, stroke, a brain tumor, and a brain metastasis.

In one aspect, the invention features a GDNF fusion polypeptide having the formula A-L-B, wherein A includes an Fc domain; L is a linker; and B includes a GDNF variant having at least 80% sequence identity (e.g., at least 85%, 90% 95% 97%, or 100% sequence identity) to a reference GDNF sequence including amino acids 118-211 of SEQ ID NO: 1.

In some embodiments, the GDNF fusion polypeptide further includes an albumin-binding peptide joined to the N-terminus of the Fc domain.

In other embodiments, the GDNF fusion polypeptide further includes a fibronectin domain joined to the N-terminus of the Fc domain.

In yet other embodiments, the GDNF fusion polypeptide further includes a human serum albumin joined to the N-terminus of the Fc domain.

In another aspect, the invention features a GDNF fusion polypeptide having the formula A-L-B, wherein A includes an albumin-binding peptide; L is a linker; and B includes a GDNF variant having at least 80% sequence identity (e.g., at least 85%, 90% 95% 97%, or 100% sequence identity) to a reference GDNF sequence including amino acids 118-211 of SEQ ID NO: 1.

In another aspect, the invention features a GDNF fusion polypeptide having the formula A-L-B, wherein A includes a fibronectin domain; L is a linker; and B includes a GDNF variant having at least 80% sequence identity (e.g., at least 85%, 90% 95% 97%, or 100% sequence identity) to a reference GDNF sequence including amino acids 118-211 of SEQ ID NO: 1.

In yet another aspect, the invention features a GDNF fusion polypeptide having the formula A-L-B, wherein A includes a human serum albumin; L is a linker; and B includes a GDNF variant having at least 80% sequence identity (e.g., at least 85%, 90% 95% 97%, or 100% sequence identity) to a reference GDNF sequence including amino acids 118-211 of SEQ ID NO: 1.

In certain embodiments of any of the above aspects, the GDNF variant consists of amino acids 92-211 of SEQ ID NO: 1 or a fragment thereof.

In some embodiments of any of the above aspects, the reference GDNF sequence includes amino acids 117-211, amino acids 110-211, amino acids 92-211, or amino acids 78-211 of SEQ ID NO: 1.

In some embodiments, the GDNF variant includes amino acid substitutions relative to wild-type human GDNF that reduce proteolysis between amino acid residues 85 and 120 of SEQ ID NO: 1. In certain embodiments, the GDNF variant includes amino acid substitutions of one or more of the following residues relative to wild-type human GDNF: R88, R89, R91, R93, R104, K106, R108, R109, R112, K114, and R116, relative to the sequence of SEQ ID NO: 1, for a non-basic amino acid.

In some embodiments, the albumin-binding peptide includes the sequence of SEQ ID NO: 2.

In other embodiments, the Fc domain does not form a dimer. In yet other embodiments, the Fc domain does not include a hinge domain.

In some embodiments, the Fc domain includes one or more of the following amino acid substitutions: T366W, T366Y, T394W, F405W, Y349T, Y349E, Y349V, L351T, L351H, L351N, L352K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, and K409I, relative to the sequence of human IgG1. The sequence of wild-type Fc domain is shown in SEQ ID NO: 3.

In some embodiments, the linker in the GDNF fusion polypeptide is a bond. In other embodiments, the linker in the GDNF fusion polypeptide is a spacer. In particular embodiments, the spacer includes the amino acid sequence GGG or the sequence of any one of SEQ ID NOs: 5-29.

In some embodiments, the fibronectin domain in the GDNF fusion polypeptide is a fibronectin type 11 domain (SEQ ID NO: 30) having amino acids 610-702 of the sequence of UniProt ID NO: P02751.

In other embodiments, a fibronectin domain is an adnectin protein.

In some embodiments, the human serum albumin in the GDNF fusion polypeptide has the sequence of UniProt ID NO: P02768 (SEQ ID NO: 31).

In some embodiments, the GDNF fusion polypeptide of the invention described herein has a serum half-life of 3 to 60 days.

In other embodiments, the GDNF fusion polypeptide binds human GDNF family receptor alpha-1 (GFRα1) with a $K_D$ of 20 to 20,000 pM.

In some embodiments, the GDNF fusion polypeptide is encoded by a single open reading frame.

In another aspect, the invention features a nucleic acid molecule encoding a GDNF fusion polypeptide described herein.

In yet another aspect, the invention features a vector containing a nucleic acid molecule encoding a GDNF fusion polypeptide described herein.

In still another aspect, the invention features a host cell that expresses a GDNF fusion polypeptide described herein, a nucleic acid molecule encoding a GDNF fusion polypeptide described herein, or a vector containing such a nucleic acid molecule.

In certain embodiment embodiments, the host cell is a mammalian cell (e.g., a Chinese hamster ovary (CHO) cell). In other embodiments, the host cell is a human embryonic kidney (HEK) (e.g., HEK293, HEK 293F), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, or HsS78Bst cell.

In yet other embodiments, the host cell is a bacterial cell (e.g., an *E. coli* cell). Examples of *E. coli* strains include, but are not limited to, *E. coli* 294 (ATCC®31,446), *E. coli* λ 1776 (ATCC®31,537, *E. coli* BL21 (DE3) (ATCC® BAA-1025), and *E. coli* RV308 (ATCC®31,608).

In another aspect, the invention features a method of preparing a GDNF fusion polypeptide of the invention. The method includes the steps of a) providing a host cell that includes a nucleic acid molecule encoding a GDNF fusion polypeptide described herein or a vector containing such a nucleic acid molecule, and b) expressing the nucleic acid molecule or vector in the host cell under conditions that allow for the production of the GDNF fusion polypeptide.

In some embodiments, the host cell used in the method of preparing any GDNF fusion polypeptide of the invention is a CHO cell. In other embodiments, the host cell used in the method is a human embryonic kidney (HEK) (e.g., HEK293, HEK 293F), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, or HsS78Bst cell.

In yet other embodiments, the host cell used in the method is a bacterial cell (e.g., an *E. coli* cell). Examples of *E. coli* strains include, but are not limited to, *E. coli* 294 (ATCC®31,446), *E. coli* λ 1776 (ATCC®31,537, *E. coli* BL21 (DE3) (ATCC® BAA-1025), and *E. coli* RV308 (ATCC®31,608).

In another aspect, the invention features a pharmaceutical composition that includes a GDNF fusion polypeptide of the invention, a nucleic acid molecule encoding a GDNF fusion polypeptide of the invention, or a vector containing a nucleic acid molecule encoding a GDNF fusion polypeptide of the invention, and one or more pharmaceutically acceptable carriers or excipients, wherein the GDNF fusion polypeptide is in a therapeutically effective amount.

In yet another aspect, the invention features a method of treating and/or preventing a metabolic disease in a subject. The method includes the step of administering to the subject a GDNF fusion polypeptide, nucleic acid molecule, vector, or pharmaceutical composition described herein.

In some embodiments, the metabolic disease is selected from the group consisting of obesity, Type-1 diabetes, and Type-2 diabetes.

In some embodiments, the metabolic disease is obesity. In other embodiments, the metabolic disease is Type-1 diabetes. In yet other embodiments, the metabolic disease is Type-2 diabetes.

In other embodiments, the method of treating and/or preventing a metabolic disease in a subject reduces body weight and/or percentage of body weight gain of the subject.

In some embodiments, the method does not affect the appetite for food intake of the subject. In other embodiments, the method reduces adiposity of the subject. In other embodiments, the method reduces adiposity of the subject without affecting lean mass. In still other embodiments, the method reduces the weights of epididymal and perirenal fat pads of the subject. In yet other embodiments, the method lowers the level of fasting insulin of the subject, increases the rate of glucose clearance of the subject, and/or improves the serum lipid profile of the subject.

In still another aspect, the invention features a method of treating and/or preventing a neurological disease in a subject. The method includes the step of administering to the subject a GDNF fusion polypeptide, a nucleic acid molecule, vector, or pharmaceutical composition described herein.

In some embodiments, the neurological disease is selected from the group consisting of schizophrenia, epilepsy, Amyotrophic lateral sclerosis (ALS), Parkinson's disease, Alzheimer's disease, Huntington's disease, anxiety, stroke, a brain tumor, and a brain metastasis.

DEFINITIONS

As used herein, the term "GDNF variant" refers to a polypeptide containing a mutant or fragment of wild-type human GDNF (defined further herein) that has longer serum half-life than wild-type human GDNF. In some embodiments, a GDNF variant has at least 80% sequence identity (e.g., 80%, 85%, 90%, 95%, 97%, or 100% sequence identity) to a reference GDNF sequence (defined further herein) having amino acids 118-211, 117-211, 110-211, 92-211, or 78-211 of SEQ ID NO: 1. In some embodiments, a GDNF variant contains amino acid substitutions relative to wild-type human GDNF that reduce proteolysis between amino acid residues 85 and 120 of SEQ ID NO: 1. Such amino acid substitutions are described in detail further herein.

As used herein, the term "wild-type human GDNF" refers to the natural form of human glial-derived neurotrophic factor (GDNF) having the sequence of SEQ ID NO: 1.

As used herein, the term "Fc domain" refers to a protein having at least 80% sequence identity (e.g., at least 85%, 90%, 95%, 97%, or 100% sequence identity) to a human Fc domain that includes at least a $C_H2$ domain and a $C_H3$ domain. Optionally, the Fc domain contains one or more amino acid substitutions that reduce or inhibit Fc domain dimerization. Optionally, the Fc domain contains a hinge domain. The Fc domain can be of immunoglobulin antibody isotype IgG, IgE, IgM, IgA, or IgD. Additionally, the Fc domain can be an IgG subtype (e.g., IgG1, IgG2a, IgG2b, IgG3, or IgG4). The Fc domain can also be a non-naturally occurring Fc domain, e.g., a recombinant Fc domain.

As used herein, the term "albumin-binding peptide" refers to an amino acid sequence of 12 to 16 amino acids that has affinity for and functions to bind serum albumin. An albumin-binding peptide can be of different origins, e.g., human, mouse, or rat. In some embodiments, an albumin-binding peptide has the sequence DICLPRWGCLW (SEQ ID NO: 2).

As used herein, the term "fibronectin domain" refers to a high molecular weight glycoprotein of the extracellular matrix, or a fragment thereof, that binds to, e.g., membrane-spanning receptor proteins such as integrins and extracellular matrix components such as collagens and fibrins. In some embodiments, a fibronectin domain is a fibronectin type III domain (SEQ ID NO: 30) having amino acids 610-702 of the sequence of UniProt ID NO: P02751. In other embodiments, a fibronectin domain is an adnectin protein.

As used herein, the term "human serum albumin" refers to the albumin protein present in human blood plasma. Human serum albumin is the most abundant protein in the blood. It constitutes about half of the blood serum protein. In some embodiments, a human serum albumin has the sequence of UniProt ID NO: P02768 (SEQ ID NO: 31).

As used herein, the term "linker" refers to a linkage between two elements, e.g., protein domains. A linker can be a covalent bond or a spacer. The term "bond" refers to a chemical bond, e.g., an amide bond or a disulfide bond, or any kind of bond created from a chemical reaction, e.g., chemical conjugation. The term "spacer" refers to a moiety (e.g., a polyethylene glycol (PEG) polymer) or an amino acid sequence (e.g., a 3-200 amino acid sequence) occurring between two polypeptides or polypeptide domains to provide space and/or flexibility between the two polypeptides or polypeptide domains. An amino acid spacer can be part of the primary sequence of a polypeptide (e.g., joined to the spaced polypeptides or polypeptide domains via the polypeptide backbone).

As used herein, the term "joined" is used to describe the combination or attachment of two or more elements, components, or protein domains, e.g., polypeptides, by means including chemical conjugation, recombinant means, and chemical bonds, e.g., disulfide bonds and amide bonds. For example, two single polypeptides can be joined to form one contiguous protein structure through chemical conjugation, a chemical bond, a peptide linker, or any other means of covalent linkage. In some embodiments, an Fc domain is joined to a GDNF variant by way of a peptide linker, wherein the N-terminus of the peptide linker is joined to the C-terminus of the Fc domain through a chemical bond, e.g., a peptide bond, and the C-terminus of the peptide linker is joined to the N-terminus of the GDNF variant through a chemical bond, e.g., a peptide bond. In other embodiments, the C-terminus of an albumin-binding peptide is joined to the N-terminus of a GDNF variant by way of a linker in the same fashion as mentioned above.

As used herein, the term "human GDNF family receptor alpha-1 (GFRα1)" refers a glycosylphosphatidylinositol (GPI) linked cell surface protein belonging to GDNF-family receptor a subtype which consists of at least four members: GFRα1, GFRα2, GFRα3, and GFRα4.

As used herein, the term "binding affinity" refers to the strength of the binding interaction between two molecules. Generally, binding affinity refers to the strength of the sum total of non-covalent interactions between a molecule and its binding partner, such as a GDNF fusion polypeptide of the invention and its target receptor (e.g., human GDNF family receptor alpha-1 (GFRα1)). Unless indicated otherwise, binding affinity refers to intrinsic binding affinity, which reflects a 1:1 interaction between members of a binding pair. The binding affinity between two molecules is commonly described by the dissociation constant ($K_D$) or the affinity constant (KA). Two molecules that have low binding affinity for each other generally bind slowly, tend to dissociate easily, and exhibit a large $K_D$. Two molecules that have high affinity for each other generally bind readily, tend to remain bound longer, and exhibit a small $K_D$. The $K_D$ of two interacting molecules may be determined using methods and techniques well known in the art, e.g., surface plasmon resonance. $K_D$ is calculated as the ratio of kon/kon. Specific illustrative embodiments are described further herein (see, e.g., Example 2). In some embodiments, a GDNF fusion polypeptide as described herein binds human GDNF family receptor alpha-1 (GFRα1) with a $K_D$ of, e.g., to 20,000 pM.

As used herein, the term "serum half-life" refers to, in the context of administering a therapeutic protein to a subject, the time required for plasma concentration of the protein in the subject to be reduced by half. The protein can be redistributed or cleared from the bloodstream, or degraded, i.e., by proteolysis. For example, a GDNF fusion polypeptide of the invention including a GDNF variant, which has the proteolytic cleavage site (i.e., amino acids 85-120 of SEQ ID NO: 1) removed or contains amino acid substitutions within the proteolytic cleavage site, has a longer serum half-life than wild-type human GDNF. The serum half-life of a protein can be measure using well-known techniques in the art, e.g., enzyme-linked immunosorbent assay (ELISA) (see, e.g., Example 4 and FIG. 2), western blot, microcopy, and mass spectrometry. In some embodiments, a GDNF fusion polypeptide as described herein has a serum half-life of, e.g., 3 to 60 days.

As used herein, the term "proteolysis" refers to the process of the breakdown of proteins into smaller polypeptides or amino acids by the hydrolysis of the peptide backbone. Wild-type human GDNF includes a potential proteolytic cleavage site between amino acid residues 85 and 120 of SEQ ID NO: 1 and thus, has a short serum half-life. The GDNF fusion polypeptides of the invention include GDNF variants having the proteolytic cleavage site deleted or amino acid substitutions within the proteolytic cleavage site such that the GDNF fusion polypeptides have reduced proteolysis and increased serum half-life compared to wild-type human GDNF. In some embodiments, the GDNF variant in a GDNF fusion polypeptide has the proteolytic cleavage site (i.e., amino acid residues 85 and 120 of SEQ ID NO: 1) deleted or altered within the proteolytic cleavage site.

As used herein, the term "non-basic amino acid" refers to an amino acid whose side chain does not have a positive charge at, e.g., physiological pH, e.g., pH 7.4. Non-basic amino acids are glycine, alanine, valine, isoleucine, leucine, phenylalanine, tryptophan, methionine, cysteine, asparagine, glutamine, serine, threonine, tyrosine, proline, aspartic acid, and glutamic acid.

As used herein, the term "single open reading frame" refers to the arrangement of nucleic acid (i.e., DNA) residues in a single chain that can be translated and expressed into a single polypeptide by the molecular machinery within a host cell. The nucleic acid residues in a single open reading frame can encode one or more genes which are arranged sequentially in series.

As used herein, the term "nucleic acid molecule" refers to polymers of nucleotides of any length, and includes DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A nucleic acid molecule may contain modified nucleotides, such as methylated nucleotides and their analogs. If present, modification to the nucleotide structure may be imparted before or after assembly of the polymer. The sequence of nucleotides may be interrupted by non-nucleotide components. A nucleic acid molecule may be further modified after synthesis, such as by conjugation with a label. Other types of modifications include, for example, substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the nucleic acid molecule(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semisolid supports. The 5' and 3' terminal OH can be phosphorylated or substituted with amines or organic capping group moieties of from 1 to 20 carbon atoms. Other hydroxyls may also be derivatized to standard protecting groups. Nucleic acid molecules can also contain analogous forms of ribose or deoxyribose sugars that are generally known in the art, including, for example, 2'-O-methyl-, 2'-O-allyl-, 2'-fluoro-, or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein the phosphate is replaced by P(O)S ("thioate"), P(S)S ("dithioate"), (O)NR$_2$ ("amidate"), P(O)R, P(O)OR', CO, or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl, or araldyl. Not all linkages in a nucleic acid molecule need to be identical. The preceding description applies to all nucleic acid molecules referred to herein, including DNA and RNA.

As used herein, the term "polypeptide" describes a single polymer in which the monomers are amino acid residues which are joined together through amide bonds. A polypeptide is intended to encompass any amino acid sequence, either naturally occurring, recombinant, or synthetically produced.

As used herein, the term "treating and/or preventing" refers to the treatment and/or prevention of a disease, e.g., a metabolic disease (e.g., obesity, Type1 and Type-2 diabetes) or a neurological disease (e.g., ALS and Parkinson's disease), using methods and compositions of the invention. Generally, treating a metabolic or neurological disease occurs after a subject has developed the metabolic or neurological disease and/or is already diagnosed with the metabolic or neurological disease. Preventing a metabolic or neurological disease refers to steps or procedures taken when a subject is at risk of developing the metabolic or neurological disease. The subject may show signs or mild symptoms that are judged by a physician to be indications or risk factors for developing the metabolic or neurological disease, but has not yet developed the disease.

As used herein, the term "metabolic disease" refers to a disease, disorder, or syndrome that is related to a subject's metabolism, such as breaking down carbohydrates, proteins, and fats in food to release energy, and converting chemicals into other substances and transporting them inside cells for energy utilization and/or storage. Some symptoms of a metabolic disease include high serum triglycerides, high low-density cholesterol (LDL), low high-density cholesterol (HDL), and/or high fasting insulin levels, elevated fasting plasma glucose, abdominal (central) obesity, and elevated blood pressure. Metabolic diseases increase the risk of developing other diseases, such as cardiovascular disease. In the present invention, metabolic diseases include, but are not limited to, obesity, Type-1 diabetes, and Type-2 diabetes.

As used herein, the term "percentage of body weight gain" refers to the percentage of gained body weight compared to a prior body weight of a subject at a prior time. The percentage of body weight gain can be calculated as follows:

$$100 \times [(\text{body weight at a later time} - \text{body weight at a prior time}) / (\text{body weight at a prior time})]$$

In the present invention, administration of a GDNF fusion polypeptide, a nucleic acid molecule encoding a GDNF fusion polypeptide, or vector containing such a nucleic acid molecule to a subject reduces the percentage of body weight gain of the subject (see, e.g., Example 5 and FIG. 3).

As used herein, the term "appetite for food intake" refers to a subject's natural desire or need for food. The appetite for food intake of a subject can be monitored by measuring the amount of food consumed after the GDNF fusion polypeptide is administered (see, e.g., Example 6 and FIG. 4). In the present invention, administration of a GDNF fusion polypeptide, a nucleic acid molecule encoding a GDNF fusion polypeptide, or vector containing such a nucleic acid molecule to a subject does not affect the subject's appetite for food intake.

As used herein, the term "adiposity" refers to the fat stored in the adipose tissue of a subject. In the present invention, administration of a GDNF fusion polypeptide, a nucleic acid molecule encoding a GDNF fusion polypeptide, or vector containing such a nucleic acid molecule to a subject reduces the subject's adiposity without affecting lean mass.

As used herein, the term "lean mass" refers to a component of body composition which includes, e.g., lean mass, body fat, and body fluid. Normally lean mass is calculated by subtracting the weights of body fat and body fluid from total body weight (see, e.g., Example 7 and FIG. 5). Typically, a subject's lean mass is between 60% and 90% of totally body weight. In the present invention, administration of a GDNF fusion polypeptide, a nucleic acid molecule encoding a GDNF fusion polypeptide, or vector containing such a nucleic acid molecule to a subject reduces the subject's adiposity (i.e., fat) without affecting lean mass.

As used herein, the term "epididymal and perirenal fat pads" refers to the tightly packed fat cells in the epididymis and around the kidney. In the present invention, administration of a GDNF fusion polypeptide, a nucleic acid molecule encoding a GDNF fusion polypeptide, or vector containing such a nucleic acid molecule to a subject reduces the weights of epididymal and perirenal fat pads of the subject.

As used herein, the term "fasting insulin" refers to a subject's level of insulin while the subject has not had any food intake for a length of time (i.e., 12-24 hours). Fasting insulin level is used in diagnosing metabolic diseases. Fasting insulin level is also used as an indication of whether a subject is at the risk of developing a metabolic disease. Normally, in a subject suffering from Type-1 diabetes, the subject's fasting insulin level is low compared to that of a healthy subject. In a subject suffering from insulin resistance (i.e., Type-2 diabetes), the subject's fasting insulin level is high compared to that of a healthy subject. In the present invention, administration of a GDNF fusion polypeptide, a nucleic acid molecule encoding a GDNF fusion polypeptide, or vector containing such a nucleic acid molecule to a subject lowers the subject's fasting insulin level.

As used herein, the term "rate of glucose clearance" refers to the rate at which glucose is being cleared from the blood. The rate of glucose clearance can be measured in a glucose tolerance test (GTT) (see, e.g., Example 8 and FIG. 6). In a GTT, a subject is given a certain amount of glucose and blood samples are taken afterward to determine how quickly it is cleared from the blood. The rate of glucose clearance can be used as a parameter in diagnosing and/or determining the risk of developing metabolic diseases such as obesity, diabetes, and insulin resistance.

As used herein, the term "serum lipid profile" refers to the measurement of the distribution of different types of lipids and lipoproteins in a subject's serum. Such measurement can be accomplished by a panel of blood tests. The types of lipids and lipoproteins in a subject's serum include, but are not limited to, cholesterol (e.g., high-density lipoprotein (HDL) and low-density lipoprotein (LDL)), triglyceride, and free fatty acid (FFA). The distribution of the different types of lipids and lipoproteins can be used as a parameter in diagnosing and/or determining the risk of developing metabolic diseases such as obesity, diabetes, and insulin resistance. High level of cholesterol, especially low-density lipoprotein, is generally regarded as an indication or risk factor for developing certain metabolic diseases, or in some severe medical cases, cardiovascular diseases. In the present invention, administration of a GDNF fusion polypeptide, a nucleic acid molecule encoding a GDNF fusion polypeptide, or vector containing such a nucleic acid molecule to a subject improves the subject's serum lipid profile such that the levels of cholesterol (especially low-density lipoprotein) and triglyceride are lowered.

As used herein, the term "hydrodynamic injection" refers to an in vivo gene delivery method where an engineered plasmid (e.g., a viral plasmid) containing a nucleic acid molecule encoding a protein of interest (e.g., a GDNF fusion polypeptide of the invention) in a large fluid volume is rapidly injected intravenously into a subject. Hydrodynamic injection uses controlled hydrodynamic pressure in veins to enhance cell permeability such that the elevated pressure from the rapid injection of the large fluid volume results in fluid and plasmid extravasation from the vein. Generally, the nucleic acid molecule is put under the control of a strong promoter in the engineered plasmid. The expression of the nucleic acid molecule is driven primarily by the liver. In mice, hydrodynamic injection is often performed by injection of the plasmid into the tail vein.

As used herein, the term "percent (%) sequence identity" refers to the percentage of amino acid (or nucleic acid) residues of a candidate sequence, e.g., the sequence of a GDNF variant, that are identical to the amino acid (or nucleic acid) residues of a reference sequence, e.g., a wild-type human GDNF, after aligning the sequences and introducing gaps, if necessary, to achieve the maximum percent sequence identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100 \times (\text{fraction of } A/B)$$

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid) sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

As used herein, the term "reference GDNF sequence" refers to a base sequence that other sequences, i.e., the sequence of a GDNF variant, can be compared to, in order to calculate the percent sequence identity of, e.g., the sequence of a GDNF variant, to the reference GDNF sequence. The total number of amino acid (or nucleic acid) residues in the reference GDNF sequence is typically used in such a comparison. In the formula described above, 100×(fraction of A/B), which calculates the percent sequence identity of a candidate sequence, e.g., the sequence of a GDNF variant, to a reference sequence, e.g., a reference GDNF sequence, A is the number of amino acid (or nucleic acid) residues in the sequence of a GDNF variant that are identical to the residues in the corresponding positions in the reference GDNF sequence, and B is the total number of amino acid (or nucleic acid) residues in the reference GDNF sequence.

As used herein, the term "host cell" refers to a vehicle that includes the necessary cellular components, e.g., organelles, needed to express proteins from their corresponding nucleic acids. The nucleic acids are typically included in nucleic acid vectors that can be introduced into the host cell by conventional techniques known in the art (e.g., transformation, transfection, electroporation, calcium phosphate precipitation, direct microinjection, etc.). A host cell may be a prokaryotic cell, e.g., a bacterial cell, or a eukaryotic cell, e.g., a mammalian cell (e.g., a CHO cell). As described herein, a host cell is used to express nucleic acid molecules encoding GDNF fusion polypeptides of the invention.

As used herein, the term "vector" refers to a nucleic acid molecule capable of transporting another nucleic acid molecule to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In some embodiments, a vector can include an internal ribosome entry site (IRES) that allows the expression of multiple GDNF fusion polypeptides. In some embodiments of the invention, viral vectors are used for in vivo gene delivery and expression of nucleic acid molecules encoding GDNF fusion polypeptides of the invention. Viral vectors for gene delivery include, but are not limited to, retroviral vectors, adenoviral vectors, poxviral vectors (e.g., vaccinia viral vectors, such as Modified Vaccinia Ankara (MVA)), adeno-associated viral vectors, and alphaviral vectors.

As used herein, the term "subject" refers to a mammal, e.g., preferably a human. Mammals include, but are not limited to, humans and domestic and farm animals, such as monkeys (e.g., a cynomolgus monkey), mice, dogs, cats, horses, and cows, etc.

As used herein, the term "pharmaceutical composition" refers to a medicinal or pharmaceutical formulation that contains an active ingredient as well as excipients and diluents to enable the active ingredient suitable for the method of administration. The pharmaceutical composition of the present invention includes pharmaceutically acceptable components that are compatible with the GDNF fusion polypeptide, the nucleic acid molecule(s) encoding the GDNF fusion polypeptide, or a vector containing such nucleic acid molecule(s). The pharmaceutical composition may be in aqueous form for intravenous or subcutaneous administration or in tablet or capsule form for oral administration.

As used herein, the term "pharmaceutically acceptable carrier" refers to an excipient or diluent in a pharmaceutical composition. The pharmaceutically acceptable carrier must be compatible with the other ingredients of the formulation and not deleterious to the recipient. In the present invention, the pharmaceutically acceptable carrier must provide adequate pharmaceutical stability to the GDNF fusion polypeptide, the nucleic acid molecule(s) encoding the GDNF fusion polypeptide, or a vector containing such nucleic acid molecule(s). The nature of the carrier differs with the mode of administration. For example, for intravenous administration, an aqueous solution carrier is generally used; for oral administration, a solid carrier is preferred.

As used herein, the term "therapeutically effective amount" refers to an amount, e.g., pharmaceutical dose, effective in inducing a desired biological effect in a subject or patient or in treating and/or preventing a patient from having a condition or disease described herein. It is also to be understood herein that a "therapeutically effective amount" may be interpreted as an amount giving a desired therapeutic effect, either taken in one dose or in any dosage or route, taken alone or in combination with other therapeutic agents.

DETAILED DESCRIPTION OF THE INVENTION

Figure 1A:
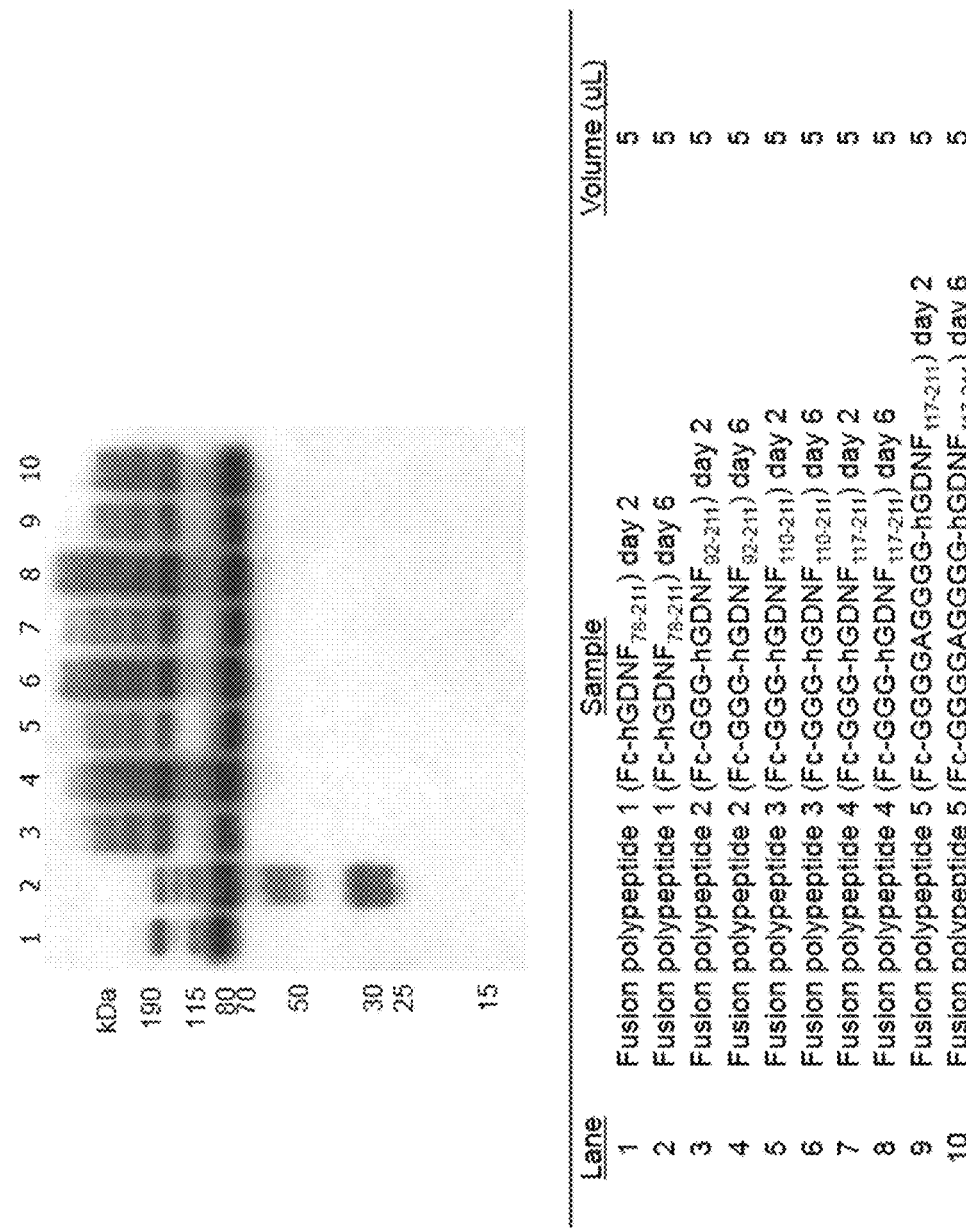
FIG. 1A is a western blot that shows the expression of five GDNF fusion polypeptides (Fusion polypeptide 1: Fc-hGDNF$_{78\text{-}211}$ (SEQ ID NO: 32), Fusion polypeptide 2: Fc-GGG-hGDNF$_{92\text{-}211}$ (SEQ ID NO: 33), Fusion polypeptide 3: Fc-GGG-hGDNF$_{110\text{-}211}$ (SEQ ID NO: 34), Fusion polypeptide 4: Fc-GGG-hGDNF$_{117\text{-}211}$ (SEQ ID NO: 35), and Fusion polypeptide 5: Fc-GGGGAGGGG (SEQ ID NO: 22)-hGDNF$_{117\text{-}211}$ (SEQ ID NO: 36)) of the invention.

The present invention features compositions and methods of preparing glial-derived neurotrophic factor (GDNF) fusion polypeptides as therapeutic proteins. The GDNF fusion polypeptides of the invention bind to human GDNF family receptor alpha-1 (GFRα1) and have long serum half-life. The invention also features pharmaceutical compositions and methods of using these GDNF fusion polypeptides to treat and/or prevent metabolic diseases such as obesity and Type-1 and Type-2 diabetes, and neurological diseases such as schizophrenia, epilepsy, Amyotrophic lateral sclerosis (ALS), Parkinson's disease, Alzheimer's disease, Huntington's disease, anxiety, stroke, a brain tumor, and a brain metastasis.

I. GDNF Fusion Polypeptides

In general, the invention features GDNF fusion polypeptides having the formula A-L-B, where A includes an Fc domain, an albumin-binding peptide, a fibronectin domain, or a human serum albumin, joined to the N-terminus of a GDNF variant directly or by way of a linker. In preferred embodiments, the GDNF fusion polypeptide is encoded by a single open reading frame. In some embodiments, when A includes an Fc domain, the GDNF fusion polypeptide of the invention further includes an albumin-binding peptide, a fibronectin domain, or a human serum albumin, joined to the N-terminus of the Fc domain directly or by way of a linker.

In certain embodiments, the GDNF fusion polypeptides of the invention have a serum half-life of 3 to 60 days. In other embodiments, the GDNF fusion polypeptides bind to human GDNF family receptor alpha-1 (GFRα1) with a $K_D$ of 20 to 20,000 pM.

II. GDNF Variants

A GDNF variant is a polypeptide containing a mutant or fragment of wild-type human GDNF (SEQ ID NO: 1). In some embodiments, a GDNF variant has at least 80% sequence identity (e.g., at least 85%, 90%, 95%, 97%, or 100% sequence identity) to a reference GDNF sequence that includes amino acids 118-211, 117-211, 110-211, 92-211, or 78-211 of SEQ ID NO: 1. The amino acid sequences of wild-type human GDNF is shown below.

```
SEQ ID NO: 1: wild-type human GDNF
  1 MKLWDVVAVC LVLLHTASAF PLPAGKRPPE APAEDRSLGR RRAPFALSSD SNMPEDYPDQ

61 FDDVMDFIQA TIKRLKRSPD KQMAVLPRRE RNRQAAAANP ENSRGKGRRG QRGKNRGCVL

121 TAIHLNVTDL GLGYETKEEL IFRYCSGSCD AAETTYDKIL KNLSRNRRLV SDKVGQACCR

181 PIAFDDDLSF LDDNLVYHIL RKHSAKRCGC I
```

Amino acids 78-211 of human GDNF form the GDNF functional domain. In certain embodiments, the GDNF variant consists of amino acids 92-211 of SEQ ID NO: 1 or a fragment thereof. In some embodiments, the GDNF variant consists of amino acids 118-211, amino acids 117-211, amino acids 110-211, amino acids 92-211, or amino acids 78-211 of SEQ ID NO: 1.

Wild-type human GDNF contains a potential proteolytic cleavage site that is approximately between amino acids 85 and 120 of SEQ ID NO: 1. This site of GDNF makes the protein prone to proteolysis and degradation. Thus, wild-type human GDNF often exhibits a short serum half-life of, e.g., less than 10 minutes (see, e.g., FIG. 4 of Boado et al., *Drug Metab Dispos.* 37:2299-304, 2009).

To improve the serum half-life of the protein, a GDNF variant can have the proteolytic cleavage site deleted. In other embodiments, a GDNF variant contains amino acid substitutions relative to wild-type human GDNF that reduce proteolysis within the potential proteolytic site (i.e., between amino acid residues 85 and 120 of SEQ ID NO: 1). Such amino acid substitutions include substituting charged amino acids, e.g., arginine and lysine, in the proteolytic cleavage site for a non-basic amino acid. Charged amino acids, e.g., arginine and lysine, between amino acids 85 and 120 that can be substituted for a non-basic amino acid include R88, R89, R91, R93, R104, K106, R108, R109, R112, K114, and R116. These amino acid residues can be substituted for non-basic amino acids such as glycine, alanine, valine, isoleucine, leucine, phenylalanine, tryptophan, methionine, cysteine, asparagine, glutamine, serine, threonine, tyrosine, proline, aspartic acid, and glutamic acid.

The GDNF fusion polypeptides including GDNF variants described above display long serum half-life, e.g., from 3 to 60 days, and maintain the desired binding affinity to GFRα1, e.g., with a $K_D$ of 20 to 20,000 pM.

III. Fc Domain

In the present invention, "Fc domain" refers to a protein having at least 80% sequence identity (e.g., at least 85%, 90%, 95%, 97%, or 100% sequence identity) to a human Fc domain that includes at least a $C_H2$ domain and a $C_H3$ domain. Optionally, the Fc domain contains one or more amino acid substitutions that reduce or inhibit Fc domain dimerization. Optionally, the Fc domain contains a hinge domain. The Fc domain can be of immunoglobulin antibody isotype IgG, IgE, IgM, IgA, or IgD. Additionally, the Fc domain can be an IgG subtype (e.g., IgG1, IgG2a, IgG2b, IgG3, or IgG4). The Fc domain can also be a non-naturally occurring Fc domain, e.g., a recombinant Fc domain.

Methods of engineering Fc domain that have reduced dimerization are known in the art. In some embodiments, one or more amino acids with large side-chains (e.g., tyrosine or tryptophan) may be introduced to the $C_H3$-$C_H3$ dimer interface to hinder dimer formation due to steric clash. In other embodiments, one or more amino acids with small side-chains (e.g., alanine, valine, or threonine) may be introduced to the $C_H3$-$C_H3$ dimer interface to remove favorable interactions. Methods of introducing amino acids with large or small side-chains in the $C_H3$ domain are described in, e.g., Ying et al. (*J Biol Chem.* 287:19399-19408, 2012), U.S. Patent Publication No. 2006/0074225, U.S. Pat. Nos. 8,216,805 and 5,731,168, Ridgway et al. (*Protein Eng.* 9:617-612, 1996), Atwell et al. (*J Mol Biol.* 270:26-35, 1997), and Merchant et al. (*Nat Biotechnol.* 16:677-681, 1998), all of which are incorporated herein by reference in their entireties.

In yet other embodiments, one or more amino acid residues in the $C_H3$ domain that make up the $C_H3$-$C_H3$ interface between two Fc domains are replaced with positively-charged amino acid residues (e.g., lysine, arginine, or histidine) or negatively-charged amino acid residues (e.g., aspartic acid or glutamic acid) such that the interaction becomes electrostatically unfavorable depending on the specific charged amino acids introduced. Methods of introducing charged amino acids in the $C_H3$ domain to disfavor or prevent dimer formation are described in, e.g., Ying et al. (*J Biol Chem.* 287:19399-19408, 2012), U.S. Patent Publication Nos. 2006/0074225, 2012/0244578, and 2014/0024111, all of which are incorporated herein by reference in their entireties.

In some embodiments of the invention, an Fc domain includes one or more of the following amino acid substitutions: T366W, T366Y, T394W, F405W, Y349T, Y349E, Y349V, L351T, L351H, L351N, L352K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, and K409I, relative to the sequence of human IgG1. In one particular embodiment, an Fc domain includes the amino acid substitution T366W, relative to the sequence of human IgG1. The sequence of wild-type Fc domain is shown in SEQ ID NO: 3.

IV. Albumin-Binding Peptide

Binding to serum protein peptides can improve the pharmacokinetics of protein pharmaceuticals, and in particular the GDNF fusion polypeptides described here may be joined with serum protein-binding peptides.

As one example, albumin-binding peptides that can be used in the methods and compositions described here are generally known in the art. In one embodiment, the albumin binding peptide includes the sequence DICLPRWGCLW (SEQ ID NO: 2).

In the present invention, albumin-binding peptides may be joined to the N-terminus of the Fc domain in a GDNF fusion polypeptide of the invention to increase the serum half-life of the GDNF fusion polypeptide. An albumin-binding peptide can be joined, either directly or through a linker, to the N-terminus of the Fc domain. In other embodiments, an albumin-binding peptide is joined, either directly or through a linker, to the N-terminus of a GDNF variant.

Albumin-binding peptides can be fused genetically to GDNF fusion polypeptides or joined to GDNF fusion polypeptides through chemical means, e.g., chemical conjugation. If desired, a spacer can be inserted between the GDNF fusion polypeptide and the albumin-binding peptide. Without being bound to a theory, it is expected that inclusion of an albumin-binding peptide in a GDNF fusion polypeptide of the invention may lead to prolonged retention of the therapeutic protein through its binding to serum albumin.

V. Fibronectin Domain

Binding to fibronectin domains can improve the pharmacokinetics of protein pharmaceuticals, and in particular the GDNF fusion polypeptides described here may be joined with fibronectin domains.

Fibronectin domain is a high molecular weight glycoprotein of the extracellular matrix, or a fragment thereof, that binds to, e.g., membrane-spanning receptor proteins such as integrins and extracellular matrix components such as collagens and fibrins. In some embodiments of the present invention, a fibronectin domain is joined to the N-terminus of the Fc domain in a GDNF fusion polypeptide of the invention to increase the serum half-life of the GDNF fusion polypeptide. A fibronectin domain can be joined, either directly or through a linker, to the N-terminus of the Fc domain. In other embodiments, a fibronectin domain is joined, either directly or through a linker, to the N-terminus of a GDNF variant.

As one example, fibronectin domains that can be used in the methods and compositions described here are generally known in the art. In one embodiment, the fibronectin domain is a fibronectin type 11 domain (SEQ ID NO: 30) having amino acids 610-702 of the sequence of UniProt ID NO: P02751. In another embodiment, the fibronectin domain is an adnectin protein.

Fibronectin domains can be fused genetically to GDNF fusion polypeptides or joined to GDNF fusion polypeptides through chemical means, e.g., chemical conjugation. If desired, a spacer can be inserted between the GDNF fusion polypeptide and the fibronectin domain. Without being bound to a theory, it is expected that inclusion of a fibronectin domain in a GDNF fusion polypeptide of the invention may lead to prolonged retention of the therapeutic protein through its binding to integrins and extracellular matrix components such as collagens and fibrins.

VI. Serum Albumin

Binding to serum albumins can improve the pharmacokinetics of protein pharmaceuticals, and in particular the GDNF fusion polypeptides described here may be joined with serum albumins.

Serum albumin is a globular protein that is the most abundant blood protein in mammals. Serum albumin is produced in the liver and constitutes about half of the blood serum proteins. It is monomeric and soluble in the blood. Some of the most crucial functions of serum albumin include transporting hormones, fatty acids, and other proteins in the body, buffering pH, and maintaining osmotic pressure needed for proper distribution of bodily fluids between blood vessels and body tissues. In preferred embodiments, serum albumin is human serum albumin. In some embodiments of the present invention, a human serum albumin is joined to the N-terminus of the Fc domain in a GDNF fusion polypeptide of the invention to increase the serum half-life of the GDNF fusion polypeptide. A human serum albumin can be joined, either directly or through a linker, to the N-terminus of the Fc domain. In other embodiments, a human serum albumin is joined, either directly or through a linker, to the N-terminus of a GDNF variant.

As one example, serum albumins that can be used in the methods and compositions described here are generally known in the art. In one embodiment, the serum albumin includes the sequence of UniProt ID NO: P02768 (SEQ ID NO: 31).

Serum albumins can be fused genetically to GDNF fusion polypeptides or joined to GDNF fusion polypeptides through chemical means, e.g., chemical conjugation. If desired, a spacer can be inserted between the GDNF fusion polypeptide and the human serum albumin. Without being bound to a theory, it is expected that inclusion of a human serum albumin in a GDNF fusion polypeptide of the invention may lead to prolonged retention of the therapeutic protein.

VII. Linkers

In the present invention, a linker is used to describe a linkage or connection between polypeptides or protein domains and/or associated non-protein moieties. In some embodiments, a linker is a linkage or connection between an Fc domain, an albumin-binding peptide, a fibronectin domain, or a human serum albumin, and a GDNF variant, for which the linker connects the C-terminus of the Fc domain, the albumin-binding peptide, the fibronectin domain, or the human serum albumin to the N-terminus of the GDNF variant, such that the two polypeptides are joined to each other in tandem series.

A linker can be a simple covalent bond, e.g., a peptide bond, a synthetic polymer, e.g., a polyethylene glycol (PEG) polymer, or any kind of bond created from a chemical reaction, e.g. chemical conjugation. In the case that a linker is a peptide bond, the carboxylic acid group at the C-terminus of one protein domain can react with the amino group at the N-terminus of another protein domain in a condensation reaction to form a peptide bond. Specifically, the peptide bond can be formed from synthetic means through a conventional organic chemistry reaction well-known in the art, or by natural production from a host cell, wherein a nucleic acid molecule encoding the DNA sequences of both proteins, e.g., an Fc domain and a GDNF variant, in tandem series can be directly transcribed and translated into a contiguous polypeptide encoding both proteins by the necessary molecular machineries, e.g., DNA polymerase and ribosome, in the host cell.

In the case that a linker is a synthetic polymer, e.g., a PEG polymer, the polymer can be functionalized with reactive chemical functional groups at each end to react with the terminal amino acids at the connecting ends of two proteins.

In the case that a linker (except peptide bond mentioned above) is made from a chemical reaction, chemical functional groups, e.g., amine, carboxylic acid, ester, azide, or other functional groups commonly used in the art, can be attached synthetically to the C-terminus of one protein and the N-terminus of another protein, respectively. The two functional groups can then react to through synthetic chemistry means to form a chemical bond, thus connecting the two proteins together. Such chemical conjugation procedures are routine for those skilled in the art.

Spacer

In the present invention, a linker between an Fc domain, an albumin-binding peptide, a fibronectin domain, or a human serum albumin, and a GDNF variant, can be an amino acid spacer including 3-200 amino acids. Suitable peptide spacers are known in the art, and include, for example, peptide linkers containing flexible amino acid residues such as glycine and serine. In certain embodiments, a spacer can contain motifs, e.g., multiple or repeating motifs, of GS, GGS, GGG, GGGGS (SEQ ID NO: 5), GGSG (SEQ ID NO: 6), or SGGG (SEQ ID NO: 7). In certain embodiments, a spacer can contain 2 to 12 amino acids including motifs of GS, e.g., GS, GSGS (SEQ ID NO: 8), GSGSGS (SEQ ID NO: 9), GSGSGSGS (SEQ ID NO: 10), GSGSGSGSGS (SEQ ID NO: 11), or GSGSGSGSGSGS (SEQ ID NO: 12). In certain other embodiments, a spacer can contain 3 to 12 amino acids including motifs of GGS, e.g., GGS, GGSGGS (SEQ ID NO: 13), GGSGGSGGS (SEQ ID NO: 14), and GGSGGSGGSGGS (SEQ ID NO: 15). In yet other embodiments, a spacer can contain 4 to 12 amino acids including motifs of GGSG (SEQ ID NO: 16), e.g., GGSG (SEQ ID NO: 17), GGSGGGSG (SEQ ID NO: 18), or GGSGGGSGGGSG (SEQ ID NO: 19). In other embodiments, a spacer can contain motifs of GGGGS (SEQ ID NO: 20), e.g., GGGGSGGGGSGGGGS (SEQ ID NO: 21). In other embodiments, a spacer can also contain amino acids other than glycine and serine, e.g., GGGGAGGGG (SEQ ID NO: 22), GENLYFQSGG (SEQ ID NO: 23), SACYCELS (SEQ ID NO: 24), RSIAT (SEQ ID NO: 25), RPACKIPNDLKQKVMNH (SEQ ID NO: 26), GGSAGGSGSGSSGGSSGASGTGTAGGTGSGSGTGSG (SEQ ID NO: 27), AAANSSIDLISVPVDSR (SEQ ID NO: 28), or GGSGGGSEGGGSEGGGSEGGGSEGGGSEGGGSGGS (SEQ ID NO: 29). In certain embodiments in the present invention, a 3- or 9-amino acid peptide spacer is used to connect an Fc domain, an albumin-binding peptide, a fibronectin domain, or a human serum albumin, and a GDNF variant in tandem series. The 3- and 9-amino acid peptide spacers consisting of sequences GGG and GGGGAGGGG (SEQ ID NO: 22), respectively. The length of the peptide spacer and the amino acids used can be adjusted depending on the two protein domains involved and the degree of flexibility desired in the final protein fusion polypeptide. The length of the spacer can be adjusted to ensure proper protein folding and avoid aggregate formation. For example, a small GDNF variant (e.g., a GDNF variant having amino acids 117-211 or 118-211 of SEQ ID NO: 1) can be joined to a longer spacer (e.g., a spacer of the sequence GGGGAGGGG (SEQ ID NO: 22)) rather than a shorter spacer (e.g., GGG).

VIII. Vectors, Host Cells, and Protein Production

The GDNF fusion polypeptides of the invention can be produced from a host cell. A host cell refers to a vehicle that includes the necessary cellular components, e.g., organelles, needed to express the polypeptides and fusion polypeptides described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, etc). The choice of nucleic acid vectors depends in part on the host cells to be used. Generally, preferred host cells are of either prokaryotic (e.g., bacterial) or eukaryotic (e.g., mammalian) origin.

Nucleic Acid Vector Construction and Host Cells

A nucleic acid sequence encoding the amino acid sequence of a GDNF fusion polypeptide of the invention may be prepared by a variety of methods known in the art. These methods include, but are not limited to, oligonucleotide-mediated (or site-directed) mutagenesis and PCR mutagenesis. A nucleic acid molecule encoding a GDNF fusion polypeptide of the invention may be obtained using standard techniques, e.g., gene synthesis. Alternatively, a nucleic acid molecule encoding a wild-type human GDNF may be truncated and/or mutated to contain specific amino acid substitutions using standard techniques in the art, e.g., QuikChange™ mutagenesis. Nucleic acid molecules can be synthesized using a nucleotide synthesizer or PCR techniques.

A nucleic acid sequence encoding a GDNF fusion polypeptide of the invention may be inserted into a vector capable of replicating and expressing the nucleic acid molecule in prokaryotic or eukaryotic host cells. Many vectors are available in the art and can be used for the purpose of the invention. Each vector may contain various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding protein of interest, and a transcription termination sequence.

In some embodiments, mammalian cells are used as host cells for the invention. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, and HsS78Bst cells. In other embodiments, E. coli cells are used as host cells for the invention. Examples of E. coli strains include, but are not limited to, E. coli 294 (ATCC®31,446), E. coli λ 1776 (ATCC®31,537, E. coli BL21 (DE3) (ATCC® BAA-1025), and E. coli RV308 (ATCC®31,608). Different host cells have characteristic and specific mechanisms for the posttranslational processing and modification of protein products. Appropriate cell lines or host systems may be chosen to ensure the correct modification and processing of the GDNF fusion polypeptide expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) *Recombinant Gene Expression: Reviews and Protocols* (*Methods in Molecular Biology*), Humana Press; 2nd ed. 2004 and Vladimir Voynov and Justin A. Caravella (eds.) *Therapeutic Proteins: Methods and Protocols* (*Methods in Molecular Biology*) Humana Press; 2nd ed. 2012.

Protein Production, Recovery, and Purification

Host cells used to produce the GDNF fusion polypeptides of the invention may be grown in media known in the art and suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. Host cells are cultured at suitable temperatures, such as from about 20° C. to about 39° C., e.g., from 25° C. to about 37° C., preferably 37° C., and $CO_2$ levels, such as 5 to 10% (preferably 8%). The pH of the medium is generally from about 6.8 to 7.4, e.g., 7.0, depending mainly on the host organism. If an inducible promoter is used in the expression vector of the invention, protein expression is induced under conditions suitable for the activation of the promoter.

Protein recovery typically involves disrupting the host cell, generally by such means as osmotic shock, sonication, or lysis. Once the cells are disrupted, cell debris may be removed by centrifugation or filtration. The proteins may be further purified. A GDNF fusion polypeptide may be purified by any method known in the art of protein purification, for example, by chromatography (e.g., ion exchange, affinity, and size-exclusion column chromatography), centrifugation, differential solubility, or by any other standard technique for the purification of proteins. For example, the protein can be isolated and purified by appropriately selecting and combining affinity columns such as Protein A column (e.g., POROS Protein A chromatography) with chromatography columns (e.g., POROS HS-50 cation exchange chromatography), filtration, ultra filtration, salting-out and dialysis procedures. In some instances, a GDNF fusion polypeptide can be conjugated to marker sequences, such as a peptide to facilitate purification. An example of a marker amino acid sequence is a hexa-histidine peptide (His-tag), which binds to nickel-functionalized agarose affinity column with micromolar affinity. Other peptide tags useful for purification include, but are not limited to, the hemagglutinin "HA" tag, which corresponds to an epitope derived from the influenza hemagglutinin protein (Wilson et al., *Cell* 37:767, 1984).

Alternatively, GDNF fusion polypeptides can be produced by the cells of a subject (e.g., a human), e.g., in the context of gene therapy, by administrating a vector (such as a viral vector (e.g., a retroviral vector, adenoviral vector, poxviral vector (e.g., vaccinia viral vector, such as Modified Vaccinia Ankara (MVA)), adeno-associated viral vector, and alphaviral vector)) containing a nucleic acid molecule encoding the GDNF fusion polypeptide of the invention. The vector, once inside a cell of the subject (e.g., by transformation, transfection, electroporation, calcium phosphate precipitation, direct microinjection, infection, etc) will promote expression of the GDNF fusion polypeptide, which is then secreted from the cell. If treatment of a disease or disorder is the desired outcome, no further action may be required. If collection of the protein is desired, blood may be collected from the subject and the protein purified from the blood by methods known in the art.

IX. Pharmaceutical Compositions and Preparations

The invention features pharmaceutical compositions that include one or more GDNF fusion polypeptides described herein. In some embodiments, pharmaceutical compositions of the invention contain one or more GDNF fusion polypeptides of the invention as the therapeutic proteins. In other embodiments, pharmaceutical compositions of the invention containing one or more GDNF fusion polypeptides may be used in combination with other agents (e.g., therapeutic biologics and/or small molecules) or compositions in a therapy. In addition to a therapeutically effective amount of the GDNF fusion polypeptide, the pharmaceutical compositions may contain one or more pharmaceutically acceptable carriers or excipients, which can be formulated by methods known to those skilled in the art. In other embodiments, pharmaceutical compositions of the invention contain nucleic acid molecules (DNA or RNA, e.g., mRNA) encoding one or more GDNF fusion polypeptides of the invention, or vectors containing such nucleic acid molecules.

Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. Pharmaceutical compositions of the invention can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Formulation methods are known in the art, see e.g., Banga (ed.) *Therapeutic Peptides and Proteins: Formulation, Processing and Delivery Systems* (2nd ed.) Taylor & Francis Group, CRC Press (2006).

The pharmaceutical compositions of the invention may be prepared in microcapsules, such as hydroxylmethylcellulose or gelatin-microcapsule and poly-(methylmethacrylate) microcapsule. The pharmaceutical compositions of the invention may also be prepared in other drug delivery systems such as liposomes, albumin microspheres, microemulsions, nano-particles, and nanocapsules. Such techniques are described in Remington: The Science and Practice of Pharmacy 22$^{th}$ edition (2012). The pharmaceutical compositions to be used for in vivo administration must be sterile. This is readily accomplished by filtration through sterile filtration membranes.

The pharmaceutical compositions of the invention may also be prepared as a sustained-release formulation. Suitable examples of sustained-release preparations include semipermeable matrices of solid hydrophobic polymers containing the GDNF fusion polypeptides of the invention. Examples of sustained release matrices include polyesters, hydrogels, polyactides (U.S. Pat. No. 3,773,919), copolymers of L-glutamic acid and y ethyl-L-glutamate, non-degradable ethylene-vinyl acetate, degradable lactic acid-glycolic acid copolymers such as LUPRON DEPOT™, and poly-D-(−)-3-hydroxybutyric acid. Some sustained-release formulations enable release of molecules over a few months, e.g., one to six months, while other formulations release pharmaceutical compositions of the invention for shorter time periods, e.g., days to weeks.

The pharmaceutical composition may be formed in a unit dose form as needed. The amount of active component, e.g., one or more GDNF fusion polypeptides of the invention, included in the pharmaceutical preparations is such that a suitable dose within the designated range is provided (e.g., a dose within the range of 0.01-30 mg/kg of body weight).

The pharmaceutical composition for gene therapy can be in an acceptable diluent, or can include a slow release matrix in which the gene delivery vehicle is imbedded. If hydrodynamic injection is used as the delivery method, the pharmaceutical composition containing a nucleic acid molecule encoding a GDNF fusion polypeptide or a vector (e.g., a viral vector) containing the nucleic acid molecule is delivered rapidly in a large fluid volume intravenously. Vectors that may be used as in vivo gene delivery vehicle include, but are not limited to, retroviral vectors, adenoviral vectors, poxviral vectors (e.g., vaccinia viral vectors, such as Modified Vaccinia Ankara), adeno-associated viral vectors, and alphaviral vectors.

X. Routes, Dosage, and Administration

Pharmaceutical compositions that contain one or more GDNF fusion polypeptides of the invention as the therapeutic proteins may be formulated for intravenous administration, parenteral administration, subcutaneous administration, intramuscular administration, intra-arterial administration, intrathecal administration, or intraperitoneal administration. The pharmaceutical composition may also be formulated for, or administered via, oral, nasal, spray, aerosol, rectal, or vaginal administration. For injectable formulations, various effective pharmaceutical carriers are known in the art. See, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986).

In some embodiments, pharmaceutical compositions that contain nucleic acid molecules encoding one or more GDNF fusion polypeptides of the invention or vectors containing such nucleic acid molecules may be administered by way of gene delivery. Methods of gene delivery are well-known to one of skill in the art. Vectors that may be used for in vivo gene delivery and expression include, but are not limited to, retroviral vectors, adenoviral vectors, poxviral vectors (e.g., vaccinia viral vectors, such as Modified Vaccinia Ankara (MVA)), adeno-associated viral vectors, and alphaviral vectors. In some embodiments, a vector can include an internal ribosome entry site (IRES) that allows the expression of multiple GDNF fusion polypeptides. In certain embodiments, mRNA molecules encoding one or more GDNF fusion polypeptides may be administered directly to a subject.

In some embodiments of the present invention, nucleic acid molecules encoding one or more GDNF fusion polypeptides or vectors containing such nucleic acid molecules may be administered using a hydrodynamic injection platform. In the hydrodynamic injection method, a nucleic acid molecule encoding a GDNF fusion polypeptide is put under the control of a strong promoter in an engineered plasmid (e.g., a viral plasmid). The plasmid is often delivered rapidly in a large fluid volume intravenously. Hydrodynamic injection uses controlled hydrodynamic pressure in veins to enhance cell permeability such that the elevated pressure from the rapid injection of the large fluid volume results in fluid and plasmid extravasation from the vein. The expression of the nucleic acid molecule is driven primarily by the liver. In mice, hydrodynamic injection is often performed by injection of the plasmid into the tail vein. In certain embodiments, mRNA molecules encoding one or more GDNF fusion polypeptides may be administered using hydrodynamic injection.

The dosage of the pharmaceutical compositions of the invention depends on factors including the route of administration, the disease to be treated, and physical characteristics, e.g., age, weight, general health, of the subject. Typically, the amount of a GDNF fusion polypeptide of the invention contained within a single dose may be an amount that effectively prevents, delays, or treats the disease without inducing significant toxicity. A pharmaceutical composition of the invention may include a dosage of a GDNF fusion polypeptide of the invention ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 0.1 to about 30 mg/kg and, in a more specific embodiment, about 1 to about 30 mg/kg. The dosage may be adapted by the physician in accordance with conventional factors such as the extent of the disease and different parameters of the subject.

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., intravenous dosage forms, subcutaneous dosage forms, and oral dosage forms (e.g., ingestible solutions, drug release capsules). Generally, therapeutic proteins are dosed at 0.1-100 mg/kg, e.g., 1-50 mg/kg. Pharmaceutical compositions that contain a GDNF fusion polypeptide of the invention may be administered to a subject in need thereof, for example, one or more times (e.g., 1-10 times or more) daily, weekly, monthly, biannually, annually, or as medically necessary. Dosages may be provided in either a single or multiple dosage regimens. The timing between administrations may decrease as the medical condition improves or increase as the health of the patient declines.

XI. Indications

The pharmaceutical compositions and methods of the invention are useful to treat and/or prevent medical conditions, such as metabolic diseases, e.g., obesity and diabetes (Type-1 and Type-2 diabetes), and neurological diseases.

In some embodiments, pharmaceutical compositions containing the GDNF fusion polypeptides of the invention may be used to prevent the development of obesity and/or to treat patients already diagnosed with obesity. For example, administration of the GDNF fusion polypeptides of the invention to a subject may help to reduce the body weight of the subject by decreasing the amount of fat, while maintaining the amount of lean mass (see, e.g., Examples 5 and 7).

In some embodiments, pharmaceutical compositions containing the GDNF fusion polypeptides of the invention may be used to prevent the development of diabetes (e.g., Type-1 and Type-2 diabetes) and/or to treat patients already diagnosed with diabetes. Patients who are likely to develop diabetes, e.g., individuals with genetic disposition, family history of diabetes, association with other autoimmune diseases, or other metabolic diseases, may be administered the GDNF fusion polypeptides of the invention prophylactically, such that the GDNF fusion polypeptides may maintain the normal function and health of β-cells and prevent or delay the autoimmune inflammatory damage to β-cells. In other embodiments, pharmaceutical compositions containing the GDNF fusion polypeptides of the invention may be administered to individuals before they would be diagnosed with diabetes (e.g., Type-1 and Type-2 diabetes) or develop clinical symptoms of diabetes, e.g., high blood glucose level, high fasting insulin level, insulin resistance, polyuria, polydipsia, and polyphagia. In some embodiments, the GDNF fusion polypeptides may be administered to patients prior to the patients needing insulin. In yet other embodiments, the administration of GDNF fusion polypeptides may delay or postpone the need for insulin treatment in diabetic patients. For example, administration of the GDNF fusion polypeptides of the invention to a subject may help to increase the rate of glucose clearance from the blood (see, e.g., Example 8).

The pharmaceutical compositions and methods of the invention are also useful to treat neurological diseases including, but are not limited to, schizophrenia, epilepsy, Amyotrophic lateral sclerosis (ALS), Parkinson's disease, Alzheimer's disease, Huntington's disease, anxiety, stroke, a brain tumor, and a brain metastasis.

EXAMPLES

Example 1—Expression of GDNF Fusion Polypeptides

For expression of the GDNF fusion polypeptides, vectors containing nucleic acid molecules encoding GDNF fusion polypeptides were transfected into Chinese hamster ovary (CHO) cells through electroporation. After protein expression, the expressed fusion polypeptides were purified from the cell culture supernatant by Protein A-based affinity column chromatography. Purified GDNF fusion polypeptides were analyzed by western blot using anti-GDNF antibody. FIG. 1A shows the expression of five GDNF fusion polypeptides:

```
Fusion polypeptide 1:
                              (SEQ ID NO: 32)
Fc-hGDNF_{78-211}

Fusion polypeptide 2:
                              (SEQ ID NO: 33)
Fc-GGG-hGDNF_{92-211}

Fusion polypeptide 3:
                              (SEQ ID NO: 34)
Fc-GGG-hGDNF_{110-211}

Fusion polypeptide 4:
                              (SEQ ID NO: 35)
Fc-GGG-hGDNF_{117-211}

Fusion polypeptide 5:
                              (SEQ ID NO: 36)
Fc-GGGGAGGGG-hGDNF_{117-211}
```

Each fusion polypeptide described above is encoded by a single open reading frame. Each of the five fusion polypeptides was analyzed on day 2 and day 6. As shown in FIG. 1A, fusion polypeptide 1, which includes the potential proteolytic cleavage site (i.e., amino acids 85-120 of SEQ ID NO: 1), appeared to generate degradation products by day 6.

Figure 1B:
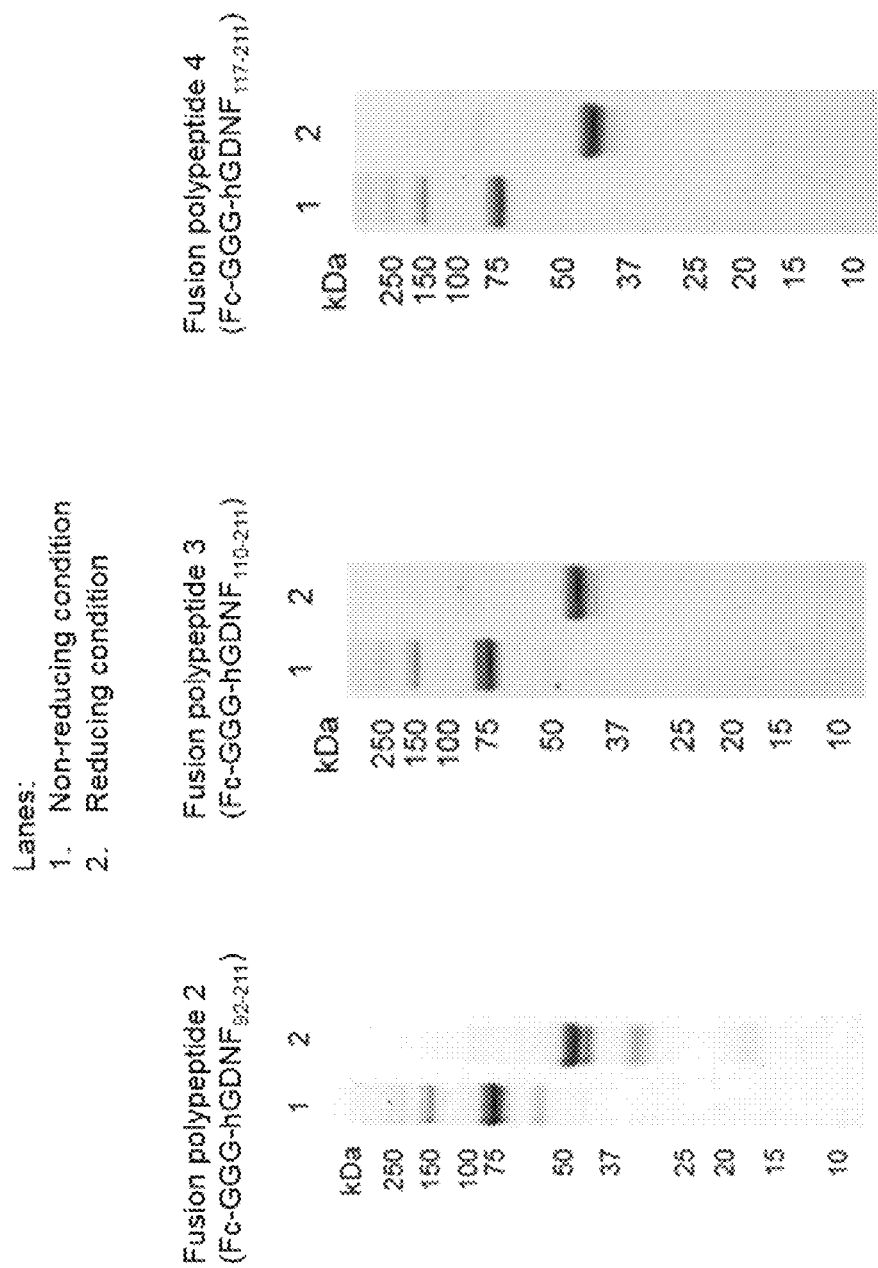
FIG. 1B is an illustration of three sodium dodecyl sulfate polyacrylamide gel electrophoresis (SDS-PAGE) gels showing the expressions of fusion polypeptide 2, 3, and 4, respectively, under either reducing or non-reducing condition.

Each of fusion polypeptides 2, 3, and 4 was also analyzed under either reducing or non-reducing condition (FIG. 1B).

Example 2—Binding Affinities

Surface Plasmon Resonance (SPR) was used to determine the binding affinities of the GDNF fusion polypeptides to GFRα1. The GDNF fusion polypeptides in this example include fusion polypeptides 2-4 as described in Example 1, as well as Fc (T366W)-GGG-hGDNF$_{117-211}$ (SEQ ID NO: 37) (fusion polypeptide 6) which has an Fc domain having the amino acid substitution T366W (relative to the sequence of human IgG1) joined to the N-terminus of the GDNF variant having amino acids 117-211 of SEQ ID NO: 1 through a GGG linker. The SPR assay was configured to capture human GFRα1, GFRα2, and GFRα3 Fc chimeras (R&D Systems) onto a CM5 chip surface using His-tag capture kit (GE Healthcare) to appropriate levels for kinetic analysis. GDNF fusion polypeptides were flowed over the immobilized GFRs to measure the kinetics of GDNF fusion polypeptide and GFR association and dissociation. The binding of various concentrations of GDNF fusion polyptides was measured in HBS-EP buffer (GE Healthcare) at a flow rate of 30 µL/min. Binding curves were fitted using Scrubber2 software to obtain apparent binding affinities and kinetic constants.

Table 1 shows that the equilibrium dissociation constant, $K_D$, of the GDNF fusion polypeptides of the invention ranged from 870 pM (fusion polypeptide 2) to 3.8 nM (fusion polypeptide 4) for binding to human GDNF family receptor alpha-1 (GFRα1) joined to an Fc domain at its C-terminus.

TABLE 1

Binding affinities of GDNF fusion polypeptides to GFRα1

|  | GFRα1-hFc $K_{D, app}$ |
| --- | --- |
| R&D hGDNF | ~900 pM |
| Fusion polypeptide 2 (Fc-GGG-hGDNF$_{92-211}$) | 160 pM |
| Fusion polypeptide 3 (Fc-GGG-hGDNF$_{110-211}$) | 870 pM |
| Fusion polypeptide 4 (Fc-GGG-hGDNF$_{117-211}$) | 3.8 nM |
| Fusion polypeptide 6 (Fc (T366W)-GGG-hGDNF$_{117-211}$) | 4.9 nM |

Example 3—GFRα1 Reporter Assay

HEK293T cells were seeded in a 96-well collagen-coated plate at a density of 20,000 cells/well in DMEM containing 10% FBS and antibiotics. Six hours later, cells were transfected with pFR-Luc (62.5 ng), pFA-ELK1 (7.5 ng), hRet (10.5 ng) and GFRα1 (4.5 ng) plasmids using Fugene 6 according to manufacturer's instructions. The next day, cells were washed once with PBS and placed in fresh DMEM containing 1% FBS for 6-8 hours. Cells were then treated with GDNF fusion polypeptides at the indicated concentration for 16 hours. Luciferase activity was determined using luciferin as substrate (Bright-Glo, Promega).

Example 4—In Vivo Serum Concentration

Figure 2:
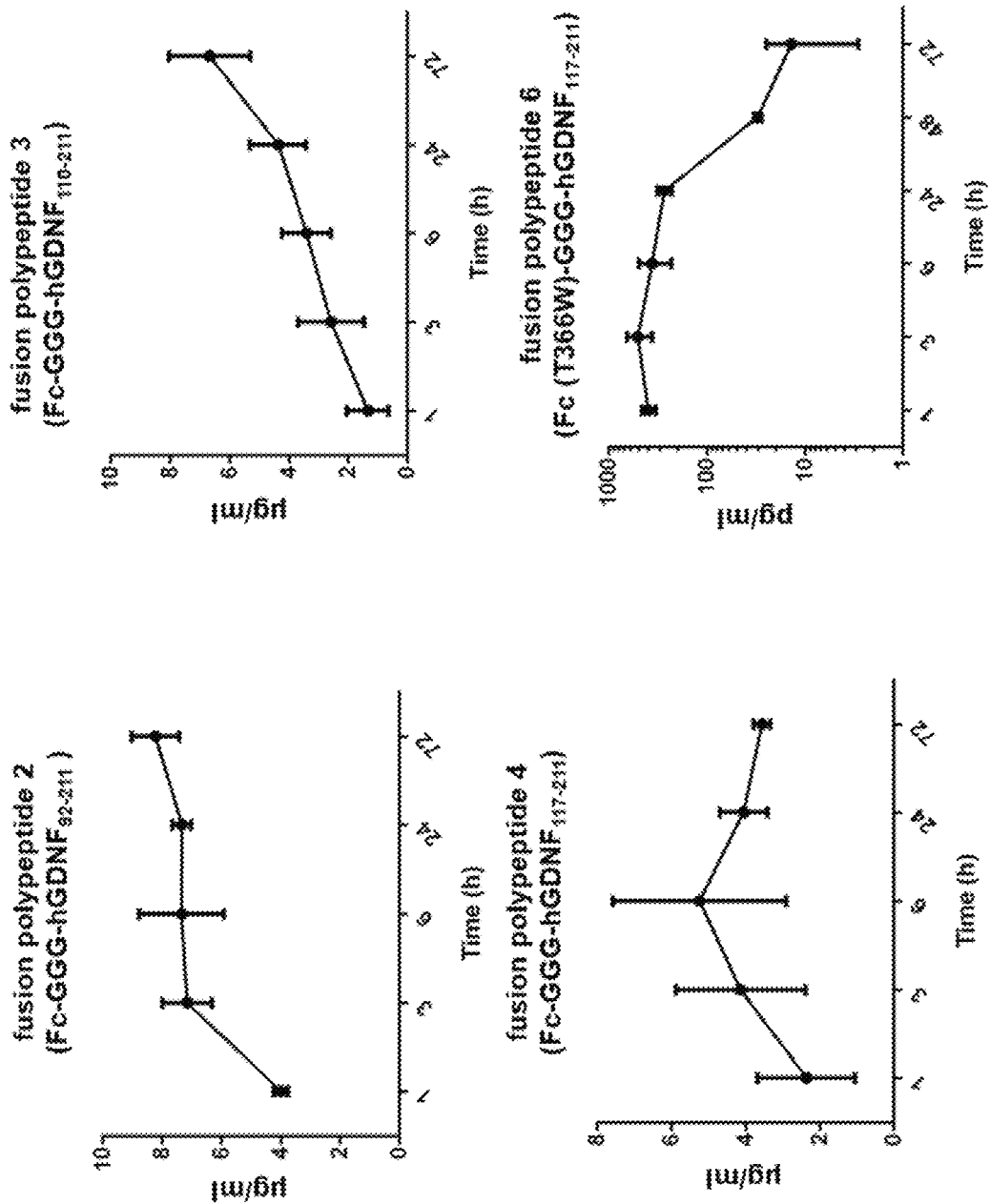
FIG. 2 is an illustration showing four graphs showing the serum concentrations of GDNF fusion polypeptides in mice.

To measure the in vivo serum concentrations of GDNF fusion polypeptides 2-4 (described in Example 1) and 6 (described in Example 2) of the invention, mice of transgenic mouse strain C57BL/6NTa were injected with 10 pg of nucleic acid molecule encoding the GDNF fusion polypeptide by way of hydrodynamic injection. Serum concentrations of the GDNF fusion polypeptide were measured using enzyme-linked immunosorbent assay (ELISA) at different time points post injection using blood samples taken from the mice. The results, shown in FIG. 2, indicate that the half-life is greater than 48 hours in mice.

Example 5—Effect of Fusion Polypeptide 6 on Body Weight

Figure 3:
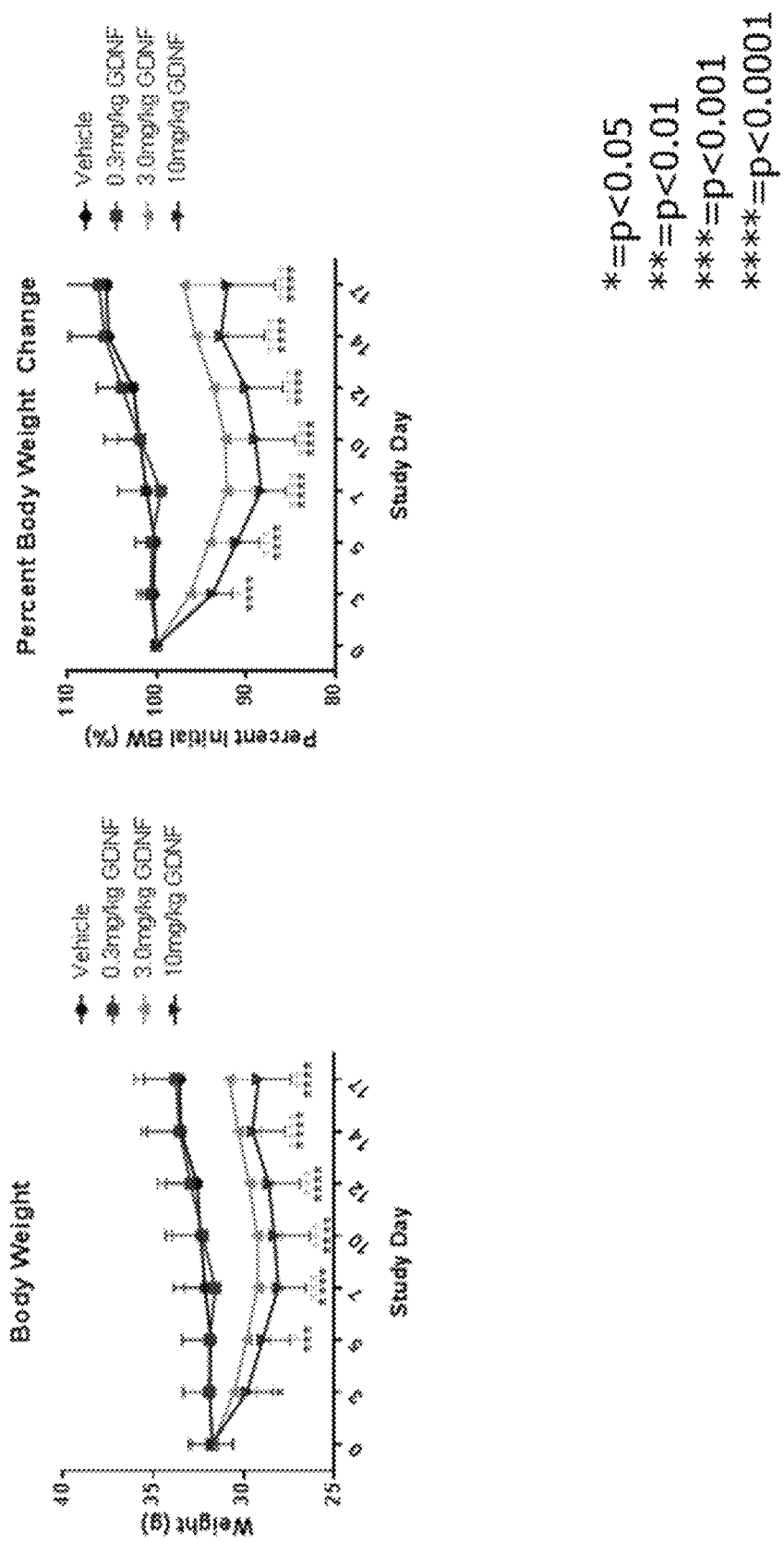
FIG. 3 is an illustration showing two graphs showing the effect of GDNF fusion polypeptide 6 on body weight.

To measure the effect of fusion polypeptide 6 (described in Example 2) on body weight, three mice of transgenic mouse strain C57BL/6NTa were injected intraperitoneally with 0.3, 3.0, or 10.0 mg/kg fusion polypeptide 6 or with phosphate buffered saline (PBS) on day 0. The average body weight of three mice was recorded every two or three days. The percent body weight change was also calculated and recorded. FIG. 3 shows that treatment with fusion polypeptide 6 reduced body weight in a dose-dependent manner.

Example 6—Effect of Fusion Polypeptide 6 on Food Intake

Figure 4:
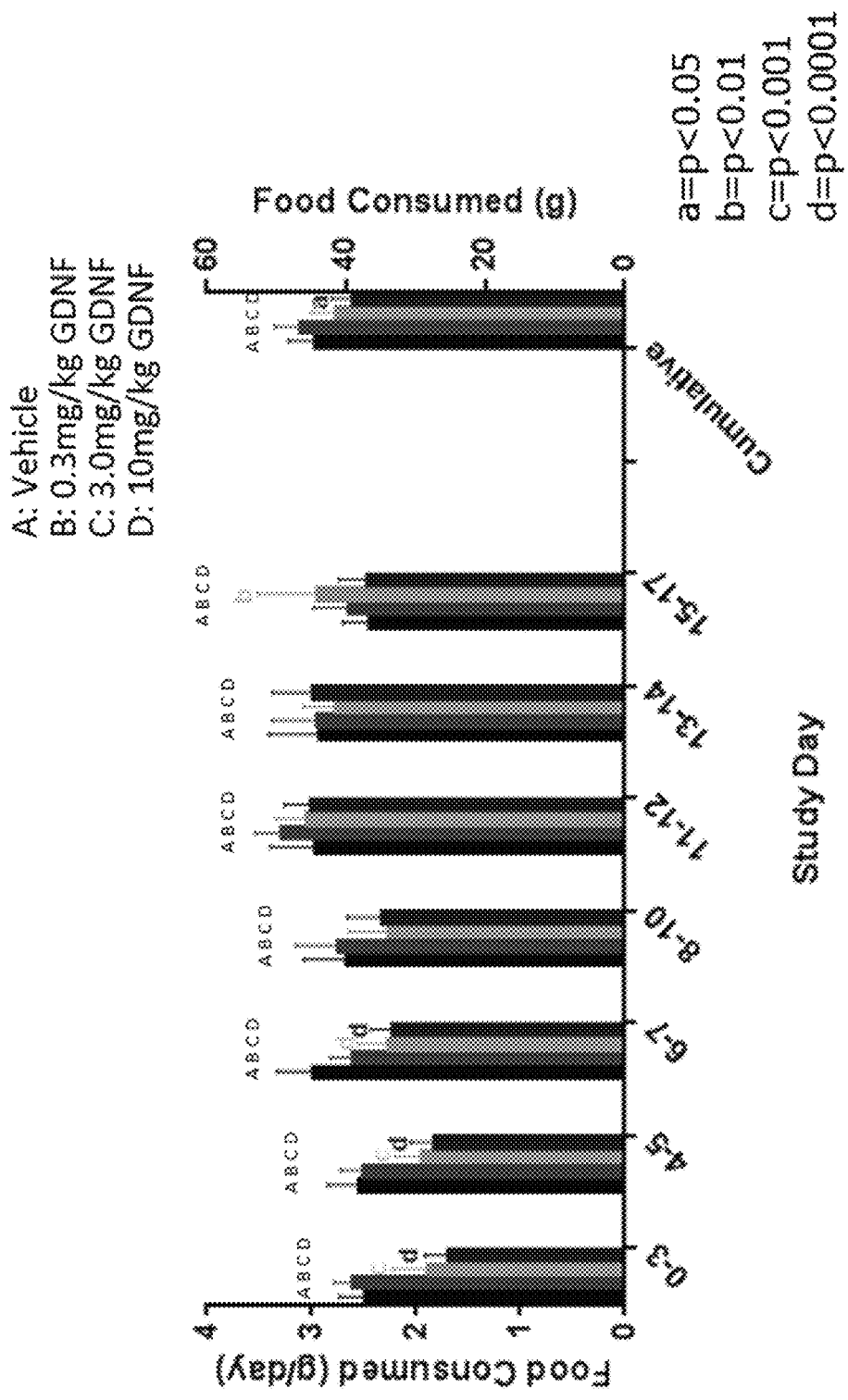
FIG. 4 is a bar graph showing the effect of GDNF fusion polypeptide 6 on food intake.

Using the same protocol as describe in Example 5, mice injected with different dosages of fusion polypeptide 6 or PBS were monitored for the amount of food intake (i.e., a high-fat diet (HFD)). The average daily amount of food intake was measured and recorded every two or three days starting on day 0. FIG. 4 shows that treatment with fusion polypeptide 6 had no significant effect on the mice's appetite for food intake.

Example 7—Effect of Fusion Polypeptide 6 on Body Composition

Using the same protocol as describe in Example 5, the change in the amount of fat, lean mass, and fluid of the mice injected with different dosages of fusion polypeptide 6 or PBS were measured on day 18 post injection.

Change from baseline = (final weight of fat, lean mass, or fluid) −

(initial weight of fat, lean mass, or fluid)

Percent change from baseline =

100 × [(final weight−initial weight)/(initial weight)]

Figure 5:
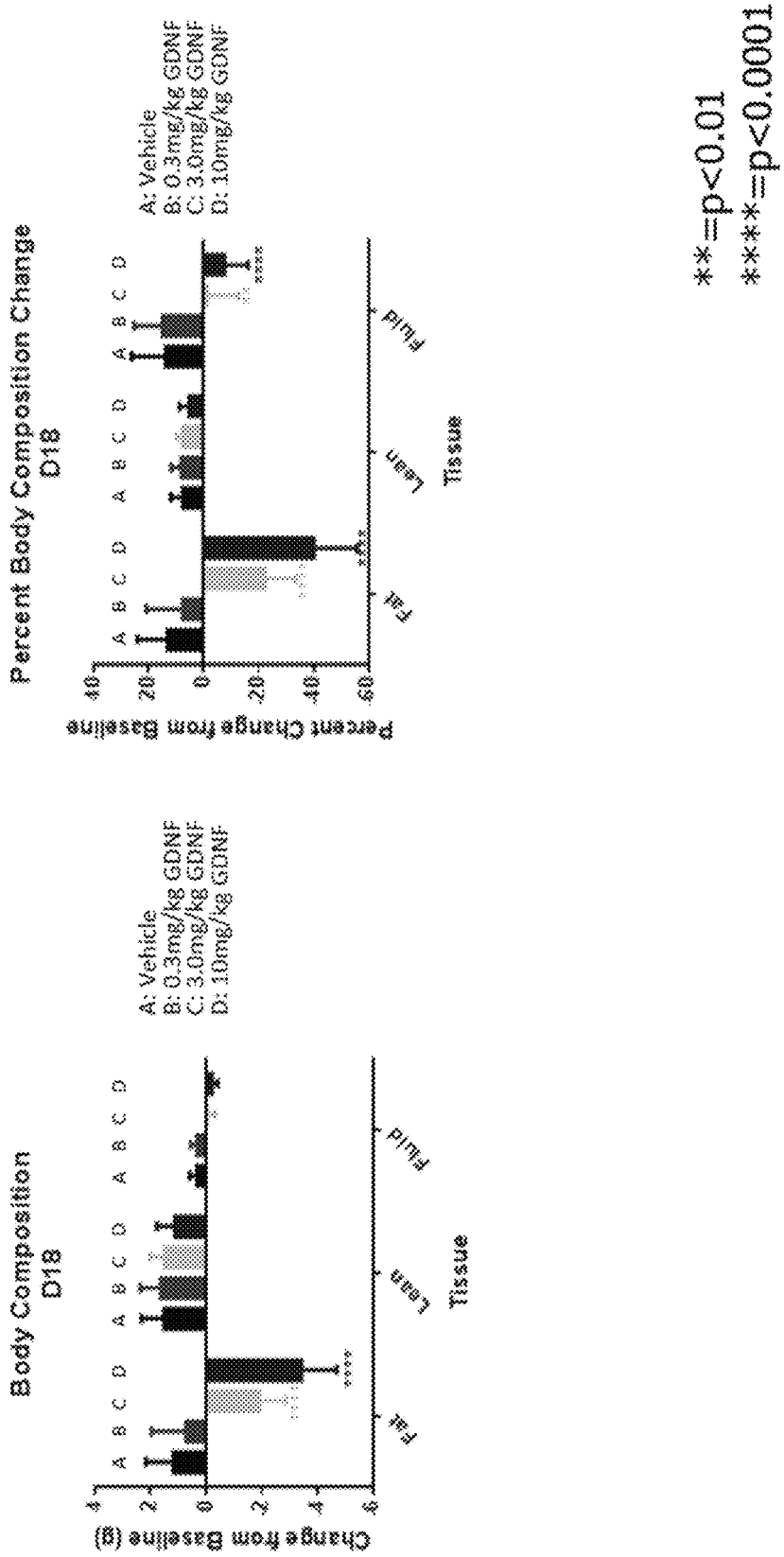
FIG. 5 includes two graphs showing the effect of GDNF fusion polypeptide 6 on body composition.

As shown in FIG. 5, treatment with fusion polypeptide 6 significantly decreased the amount of fat without affecting lean mass in the body, indicating that the weight loss of the mice is fully attributable to a reduction in adiposity.

Example 8—Effect of Fusion Polypeptide 6 on Rate of Glucose Clearance

Using the same protocol as describe in Example 5, mice injected with different dosages of fusion polypeptide 6 or PBS were subjected to a glucose tolerance test (GTT). Following a 5-hour fast, fasting blood glucose levels of mice were measured and recorded. Mice were the injected intraperitoneally with D-glucose at a dose of 2 g/kg body weight. Blood glucose measurements were taken at 15, 30, 60, 90 and 120 minutes post glucose injection. All samples were taken from tail vein bleeds and measured with a glucometer.

Figure 6:
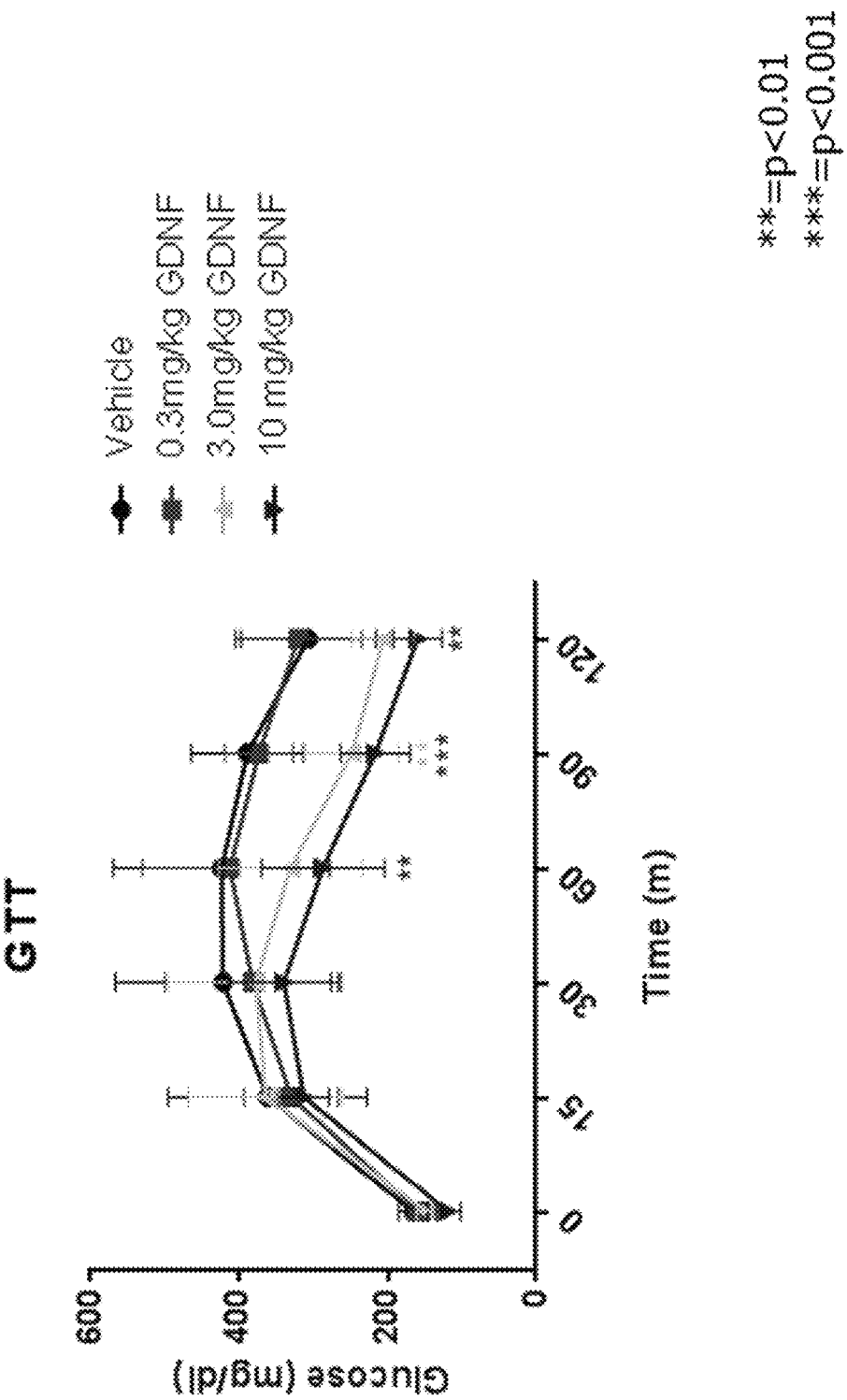
FIG. 6 is a graph showing the effect of GDNF fusion polypeptide 6 on the rate of glucose clearance.

As shown in FIG. 6, treatment with fusion polypeptide 6 significantly improved the rate of glucose clearance. The level of serum glucose in mice injected with 10 mg/kg fusion polypeptide 6 was back to the initial level of serum glucose before GTT after 2 hours.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Other embodiments are within the following claims.

The invention claimed is:

1. A method of treating and/or preventing a neurological disease in a subject, said method comprising administering to said subject a glial-derived neurotrophic factor (GDNF) fusion polypeptide consisting of the formula A-L-B, wherein
A is an Fc domain;
L is a linker; and
B has at least 95% sequence identity to a GDNF variant, wherein the sequence of the GDNF variant is (a) the sequence of amino acids 92-211 of SEQ ID NO: 1 or (b) a fragment of the sequence of amino acids 92-211 of SEQ ID NO: 1 comprising amino acids 118-211 of SEQ ID NO: 1.

2. The method of claim 1, wherein said Fc domain does not form a dimer.

3. The method of claim 1, wherein said Fc domain does not comprise a hinge domain.

4. The method of claim 1, wherein said linker comprises amino acid sequence GGG or the sequence of any one of SEQ ID NOs: 5-29.

5. The method of claim 1, wherein said neurological disease is selected from the group consisting of schizophrenia, epilepsy, Amyotrophic lateral sclerosis, Parkinson's disease, Alzheimer's disease, Huntington's disease, anxiety, stroke, a brain tumor, and a brain metastasis.

6. The method of claim 1, wherein B has at least 97% sequence identity to said GDNF variant, wherein the sequence of the GDNF variant is (a) the sequence of amino acids 92-211 of SEQ ID NO: 1 or (b) a fragment of the sequence of amino acids 92-211 of SEQ ID NO: 1 comprising amino acids 118-211 of SEQ ID NO: 1.

7. The method of claim 1, wherein the sequence of B is (a) the sequence of amino acids 92-211 of SEQ ID NO: 1 or (b) a fragment of the sequence of amino acids 92-211 of SEQ ID NO: 1 comprising amino acids 118-211 of SEQ ID NO: 1.

8. The method of claim 1, wherein the sequence of said GDNF variant is the sequence of amino acids 110-211 of SEQ ID NO: 1.

9. The method of claim 8, wherein the sequence of B is the sequence of amino acids 110-211 of SEQ ID NO: 1.

10. The method of claim 1, wherein the sequence of said GDNF variant is the sequence of amino acids 117-211 of SEQ ID NO: 1.

11. The method of claim 10, wherein the sequence of B is the sequence of amino acids of 117-211 of SEQ ID NO: 1.

12. The method of claim 1, wherein the sequence of said GDNF variant is the sequence of amino acids 118-211 of SEQ ID NO: 1.

13. The method of claim 12, wherein the sequence of B is the sequence of amino acids 118-211 of SEQ ID NO: 1.

14. The method of claim 1, wherein the GDNF fusion polypeptide is produced by expression in a mammalian cell.

15. The method of claim 1, wherein the linker is a 3-9 amino acid peptide spacer.

* * * * *